(12) United States Patent
List et al.

(10) Patent No.: US 10,550,146 B2
(45) Date of Patent: Feb. 4, 2020

(54) METHODS FOR THE PREPARATION OF OBETICHOLIC ACID AND DERIVATIVES THEREOF

(71) Applicant: Intercept Pharmaceuticals, Inc., New York, NY (US)

(72) Inventors: Benjamin List, Muelheim an de Ruhr (DE); Chandra Kanta De, Muelheim an der Ruhr (DE); Qinggang Wang, Qingdao (CN)

(73) Assignee: Intercept Pharmaceuticals, Inc., New York, NY (US)

( * ) Notice: Subject to any disclaimer, the term of this patent is extended or adjusted under 35 U.S.C. 154(b) by 0 days.

(21) Appl. No.: 16/094,535

(22) PCT Filed: Apr. 18, 2017

(86) PCT No.: PCT/US2017/028130
§ 371 (c)(1),
(2) Date: Oct. 18, 2018

(87) PCT Pub. No.: WO2017/184598
PCT Pub. Date: Oct. 26, 2017

(65) Prior Publication Data
US 2019/0211052 A1 Jul. 11, 2019

Related U.S. Application Data

(60) Provisional application No. 62/324,405, filed on Apr. 19, 2016.

(51) Int. Cl.
*C07J 9/00* (2006.01)
*C07J 31/00* (2006.01)

(52) U.S. Cl.
CPC ............ *C07J 9/005* (2013.01); *C07J 9/00* (2013.01); *C07J 31/006* (2013.01)

(58) Field of Classification Search
CPC ... C07J 9/005; C07J 9/00; C07J 31/006; C07J 51/00
See application file for complete search history.

(56) References Cited

U.S. PATENT DOCUMENTS

| | | | |
|---|---|---|---|
| 1,895,945 | A | 1/1933 | Semon et al. |
| 2016/0074419 | A1 | 3/2016 | Steiner et al. |

FOREIGN PATENT DOCUMENTS

| | | | | |
|---|---|---|---|---|
| CN | 106046095 | A | 10/2016 | |
| WO | WO 2002/072598 | A1 | 9/2002 | |
| WO | WO 2006/122977 | A2 | 11/2006 | |
| WO | WO-2006122977 | A2 * | 11/2006 | ............ C07J 9/005 |
| WO | WO 2013/192097 | A1 | 12/2013 | |
| WO | WO 2014/066819 | A1 | 5/2014 | |
| WO | WO-2014066819 | A1 * | 5/2014 | ................ C07J 9/00 |

OTHER PUBLICATIONS

Zaragoza Dorwald, Side Reactions in Organic Synthesis, 2005, WILEY-VCH Verlag GmbH & Co. KGaA, Weinheim, Preface. p. IX. (Year: 2005).*
Paraldehyde, Wikipedia, Paraldehyde, pp. 1-7 recovered from https://en.wikipedia.org/wiki/Paraldehyde on May 21, 2019 (Year: 2019).*
Yamamto et al, Tetrahedron, New reaction and new catalyst-a personal perspective, 2007, 63, pp. 8377-8412. (Year: 2007).*
Khurana, JM et al. "Facile Hydrolysis of Esters with KOH-Methanol at Ambient Temperature", Monatshefte fur Chemie, vol. 135, 2004, pp. 83-87.
Marx, A et al. "Aluminum Bis(trifluoromethylsulfonyl)amides: New Highly Efficient and Remarkably Versatile Catalysts for C—C Bond Formation Reactions. Erschienen", Angewandte Chemie International Edition, vol. 39, 2000, pp. 178-181.

(Continued)

*Primary Examiner* — Paul A Zucker
(74) *Attorney, Agent, or Firm* — Michelle Iwamoto-Fan; Intercept Pharmaceuticals, Inc.

(57) ABSTRACT

The present application relates to a safe method of preparing a bile acid derivative or a pharmaceutical acceptable salt, solvate, or amino acid conjugate thereof, on a large scale from 7-keto lithocholic acid (KLCA), comprising reacting Compound 2 with paraldehyde to form Compound 3 at a temperature between 10° C. and 30° C.:

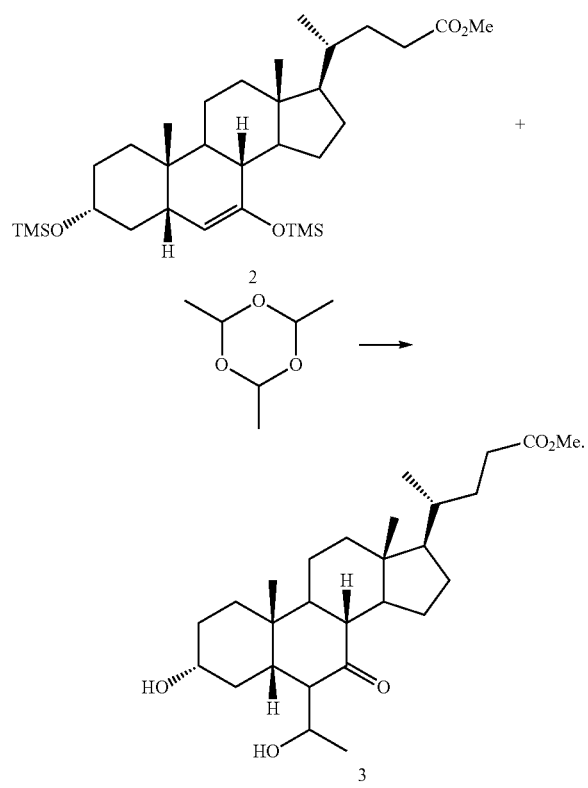

20 Claims, No Drawings

(56) References Cited

OTHER PUBLICATIONS

Otth, E. "Caught in the ACTivation of Hypervalent Iodine Trifluoromethylating Reagents", ETH Zurich Research Collection, 2015, pp. 1-186. Retrieved from the Internet: http://e-collection.library.ethz.ch/eserv/eth:47500/eth-47500-02.pdf.
Yamamoto, H. "New reaction and new catalyst—a personal perspective", Tetrahedron, vol. 63, 2007, pp. 8377-8412.
Weissermel et al. Industrial Organic Chemistry, 3rd ed. 1997, p. 188.

* cited by examiner

METHODS FOR THE PREPARATION OF OBETICHOLIC ACID AND DERIVATIVES THEREOF

BACKGROUND

Farnesoid X receptor (FXR) is a nuclear receptor that functions as a bile acid sensor controlling bile acid homeostasis. FXR is expressed in various organs and shown to be involved in the regulation of many diseases and conditions, such as liver diseases, lung diseases, renal diseases, intestinal diseases, and heart diseases, and biological processes, including glucose metabolism, insulin metabolism, and lipid metabolism.

Numerous bile acid derivatives are FXR agonists, and are able to regulate FXR-mediated diseases and conditions. Obeticholic acid (i.e., OCA, 6-ethylchenodeoxycholic acid, or 6-ECDCA) possesses potent FXR agonistic activity. Various methods of synthesizing OCA have been described, for example, in WO2002/072598, WO2006/122977, and more recently WO2013/192097. However, there are still needs for improved processes that are capable of preparing OCA and derivatives thereof with an increased yield, reduced cost, and good safety profile. The present application addresses such needs.

SUMMARY

The present application relates to methods of preparing obeticholic acid (OCA) and derivatives thereof. In one aspect, the present application relates to a method of preparing obeticholic acid (OCA):

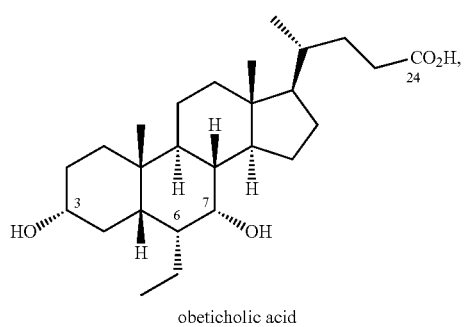

obeticholic acid or a pharmaceutical acceptable salt, solvate, or amino acid conjugate thereof, comprising:

a) reacting Compound 2 with paraldehyde to form Compound 3:

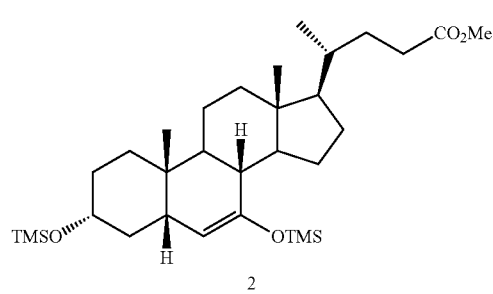

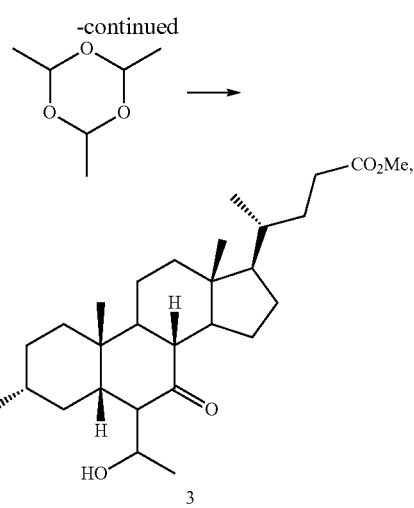

b) reacting Compound 3 with a base to form Compound 4:

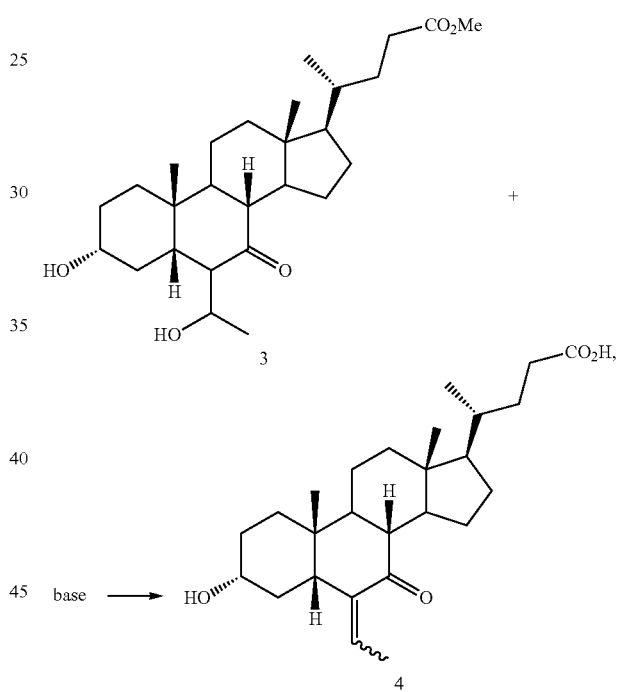

c) hydrogenating Compound 4 to form Compound 5:

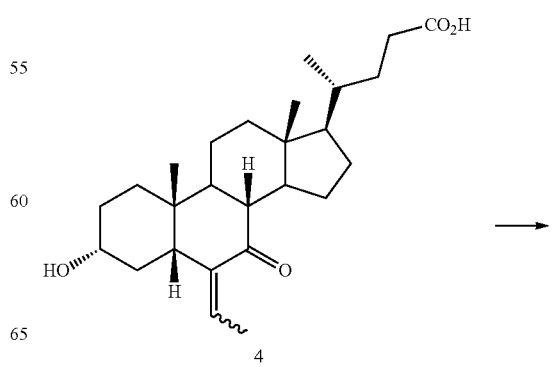

-continued

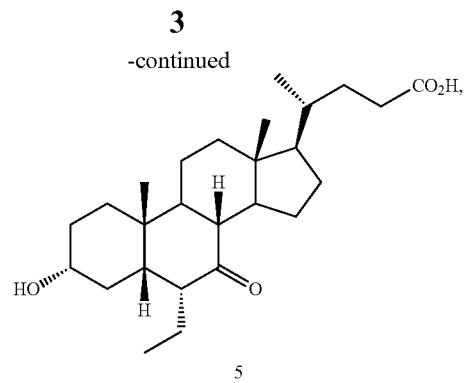

5 and d) reducing the keto group at the C-7 position of Compound 5 to form OCA:

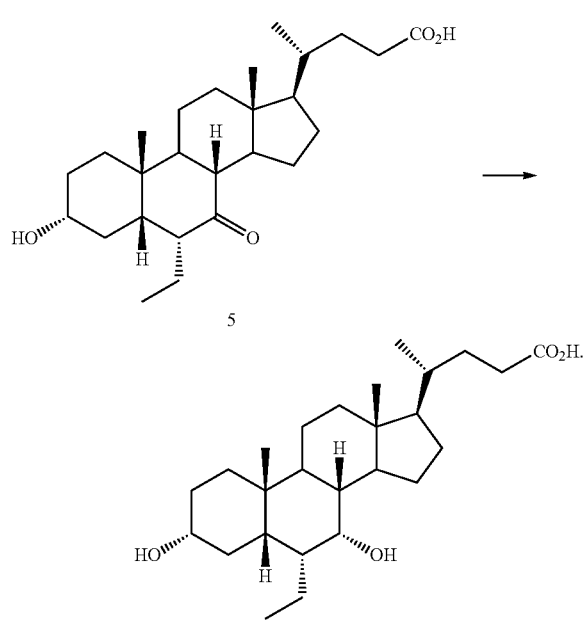

The present application further relates to a method of preparing Compound 3, comprising reacting Compound 2 with paraldehyde to form Compound 3:

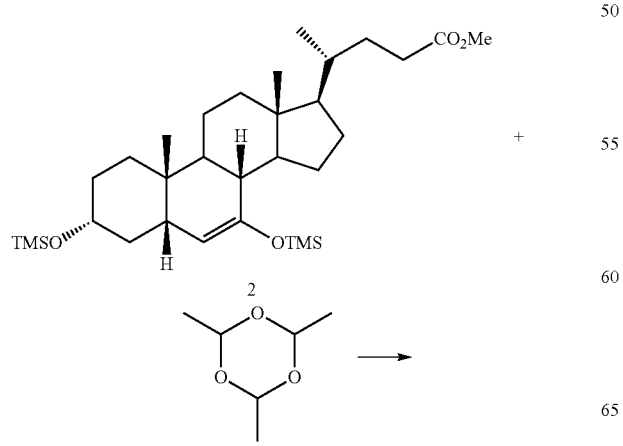

-continued

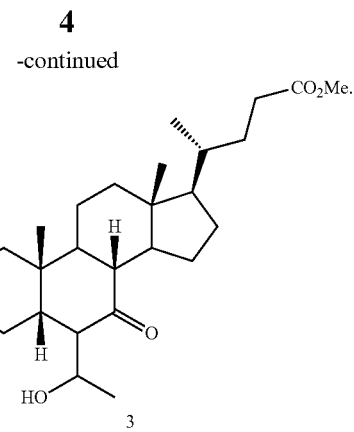

3

The present application also relates to a method of preparing Compound 4, comprising reacting Compound 3 with a base to form Compound 4:

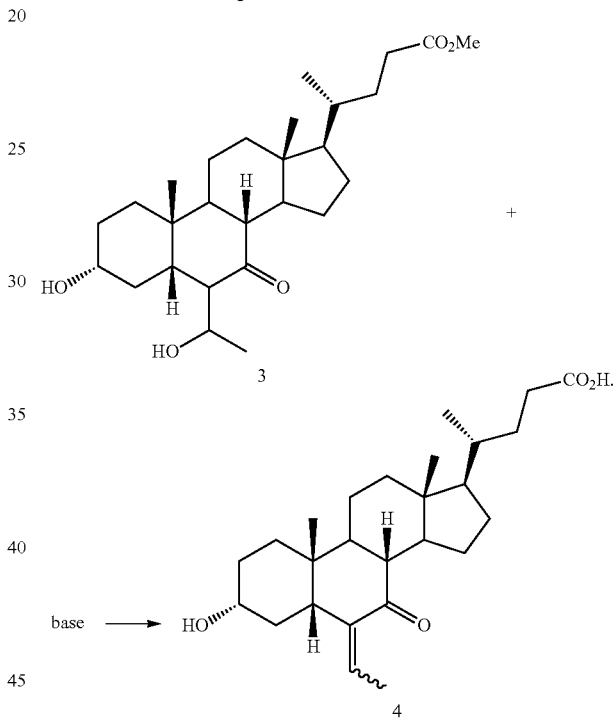

The present application also relates to a method of preparing Compound 5, comprising hydrogenating Compound 4 to form Compound 5:

-continued

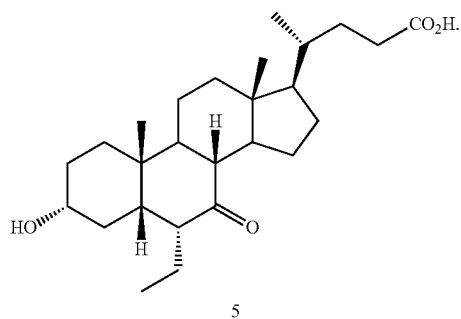

5

The present application also relates to a method of preparing OCA, comprising reducing the keto group at the C-7 position of Compound 5 to form OCA:

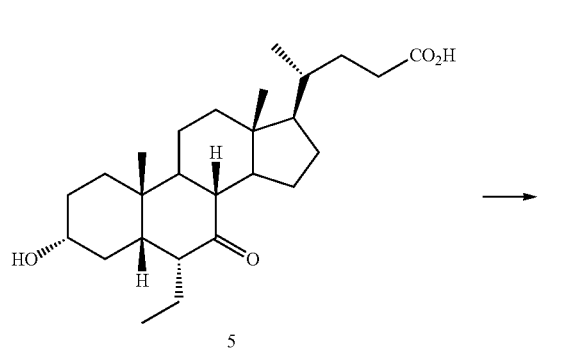

OCA

The present application also relates to a method of preparing 6α-ethyl-3α,7α-23-trihydroxy-24-nor-5β-cholan-23-sulfate (Compound 11):

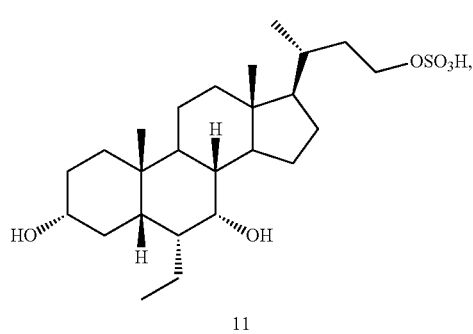

11 or a pharmaceutical acceptable salt, solvate, or amino acid conjugate thereof, comprising:

e) esterifying OCA to form Compound 6:

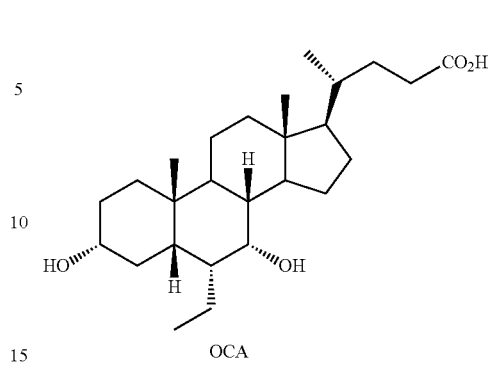

OCA

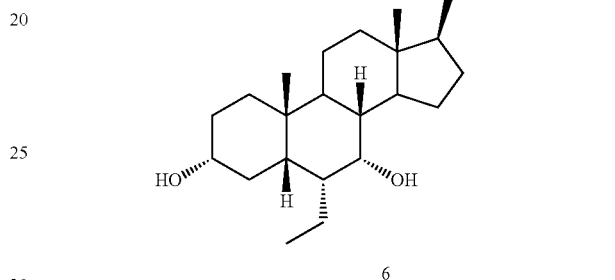

6 f) converting Compound 6 to form Compound 7:

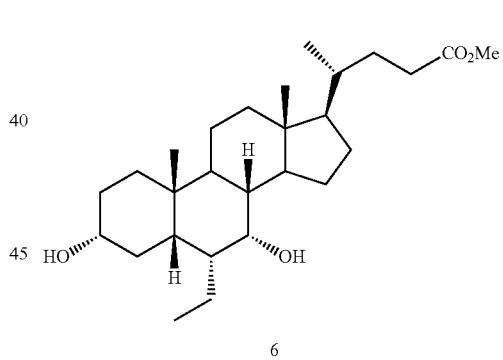

6

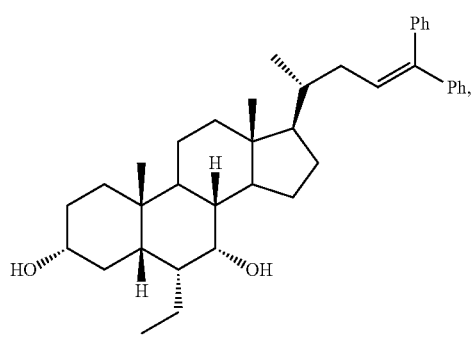

7 g) converting Compound 7 to form Compound 8:

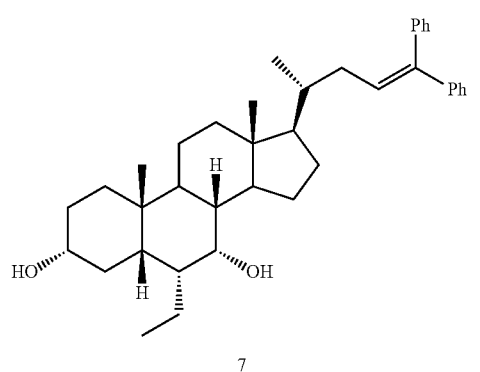

7

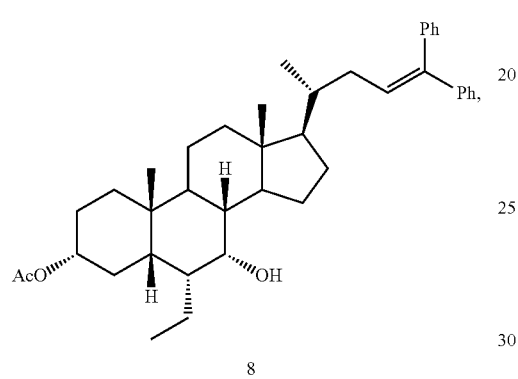

8 h) converting Compound 8 to form Compound 9:

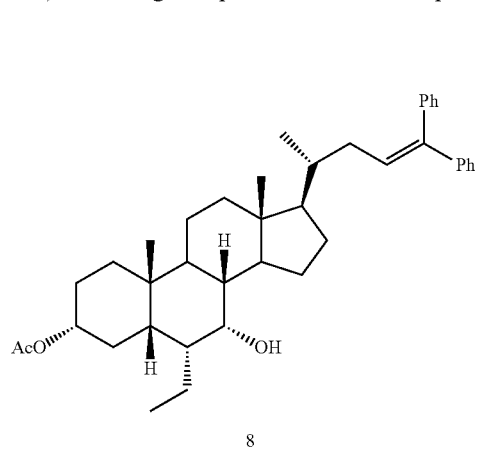

8

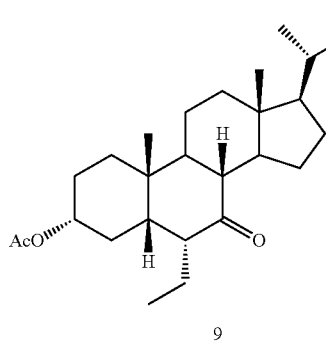

9 i) converting Compound 9 to form Compound 10:

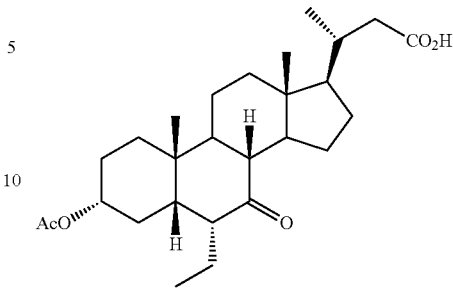

9

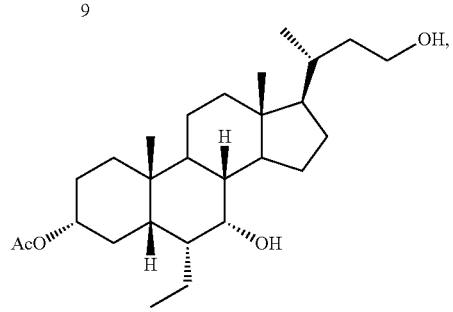

10 and j) converting Compound 10 to form Compound 11:

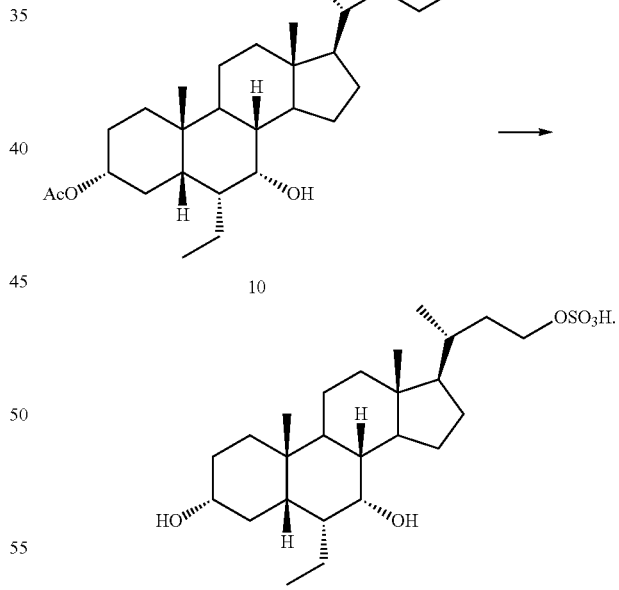

10

11

DETAILED DESCRIPTION

Methods of Preparation

The present application provides a method of preparing OCA, or a pharmaceutical acceptable salt, solvate, or amino acid conjugate thereof, comprising reacting Compound 2 with paraldehyde to form Compound 3:

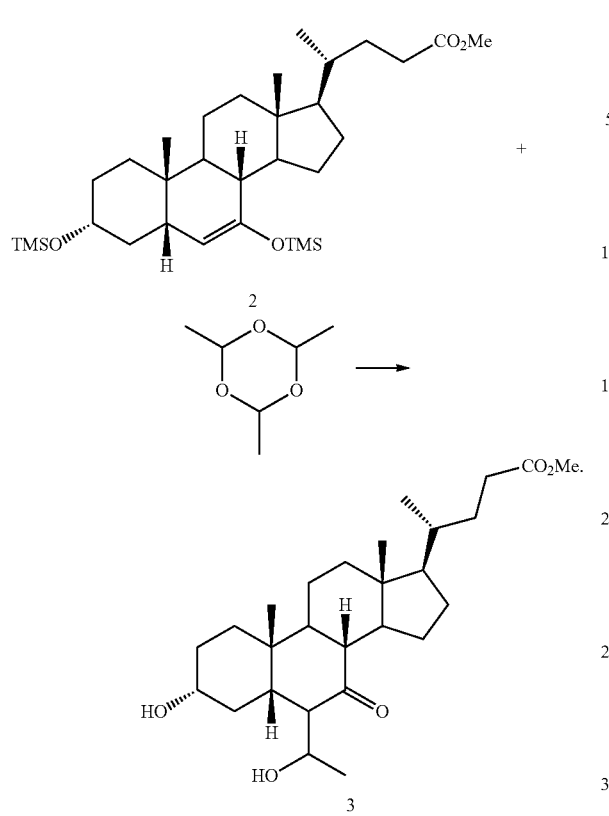

In one embodiment, the reaction is conducted in the presence of a triflimide (i.e., $(CF_3S(O)_2)_2NR$ or $(Tf)_2NR$) catalyst, wherein R is H, $C_1$-$C_3$ alkyl, or tri-$C_1$-$C_3$ alkylsilyl. In one embodiment, the triflimide catalyst is selected from $(Tf)_2NH$, $(Tf)_2N$—($C_1$-$C_3$ alkyl), and $(Tf)_2N$-tri-$C_1$-$C_3$ alkylsilyl. In one embodiment, the triflimide catalyst is $(Tf)_2NH$. In one embodiment, the triflimide catalyst is selected from $(Tf)_2NCH_3$, $(Tf)_2NCH_2CH_3$, and $(Tf)_2NCH_2CH_2CH_3$. In one embodiment, the triflimide catalyst is selected from $(Tf)_2N$-trimethylsilyl, $(Tf)_2N$-triethylsilyl, and $(Tf)_2N$-tripropylsilyl. In one embodiment, the triflimide catalyst is $(Tf)_2N$-trimethylsilyl (i.e., $(Tf)_2NTMS$). In one embodiment, the reaction is conducted in the presence of $TiCl_4$. In one embodiment, the reaction is conducted in the presence of $BF_3$. In one embodiment, the reaction is conducted the reaction is conducted in the presence of $Zn(OTf)_2$, $FeCl_3$, $SnCl_4$, or $CeCl_3 \cdot NaI$.

In one embodiment, the reaction is conducted under inert air. In one embodiment, the inert air is Ar.

In one embodiment, the reaction is conducted at a temperature between about 0° C. and about 50° C., between about 0° C. and about 40° C., between about 0° C. and about 35° C., between about 5° C. and about 35° C., between about 5° C. and about 30° C., between about 10° C. and about 30° C., between about 10° C. and about 25° C., between about 15° C. and about 25° C., or between about 20° C. and about 25° C.

In one embodiment, the reaction is conducted for about 10 min to 4 hr, about 10 min to 3 hr, about 10 min to 2 hr, about 20 min to 2 hr, about 20 min to 90 min, about 20 min to 60 min, about 20 min to 40 min, or about 30 min.

In one embodiment, the reaction is conducted in neat paraldehyde. In one embodiment, the molar ratio of paraldehyde to Compound 2 is between about 3:1 and about 6:1.

In one embodiment, the molar ratio of paraldehyde to Compound 2 is between about 3:1 and about 5:1. In one embodiment, the molar ratio of paraldehyde to Compound 2 is about 4:1.

In one embodiment, the reaction is stirred.

In one embodiment, Compound 3 is filtered after the reaction is completed.

In one embodiment, the method of the present application further comprises reacting Compound 3 with a base to form Compound 4:

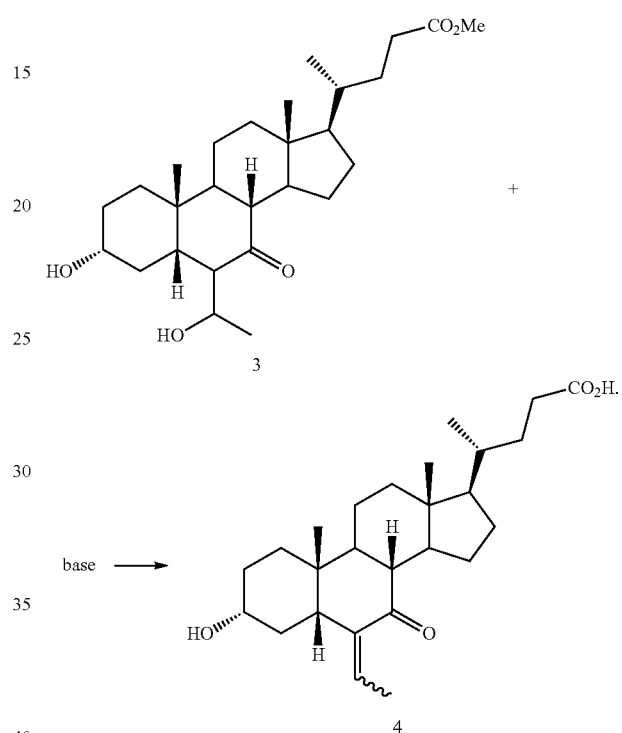

In one embodiment, the base is selected from metal hydroxide, $C_1$-$C_6$ alkoxide, and metal hydride. In one embodiment, the base is a metal hydroxide. In one embodiment, the metal hydroxide is sodium hydroxide or potassium hydroxide. In one embodiment, the base is an alkoxide (e.g., methoxide, ethoxide, propoxide, iso-propoxide, butoxide, iso-butoxide, tert-butoxide, pentoxide, iso-pentoxide, tert-pentoxide, and hexyloxide). In one embodiment, the base is a metal hydride. In one embodiment, the metal hydride is sodium hydride or potassium hydride.

In one embodiment, the reaction is conducted in a solvent selected from methanol, ethanol, propanol, isopropanol, water, and a mixture thereof. In one embodiment, the reaction is conducted in a mixture of ethanol and water at an ethanol/water ratio of between 1:3 to 3:1, between 1:2 to 2:1, between 1:1.5 to 1.5:1, between 1:1.2 to 1.2:1, or about 1:1 (vol/vol).

In one embodiment, the reaction mixture is heated. In one embodiment, the reaction mixture is heated to about 40° C. to about 50° C., about 50° C. to about 60° C., about 60° C. to about 70° C., or about 70° C. to about 80° C. In one embodiment, the reaction mixture is heated to about 75° C.

In one embodiment, the reaction is conducted for about 1 hr to 8 hr, about 1 hr to 6 hr, about 1 hr to 4 hr, about 1 hr to 3 hr, about 1.5 hr to 2.5 hr, or about 2 hr.

In one embodiment, the reaction mixture is cooled after the reaction is completed. In one embodiment, the reaction is cooled to a temperature between about 0° C. and about 50° C., between about 0° C. and about 40° C., between about 0° C. and about 35° C., between about 5° C. and about 35° C., between about 5° C. and about 30° C., between about 10° C. and about 30° C., between about 10° C. and about 25° C., between about 15° C. and about 25° C., or between about 20° C. and about 25° C.

In one embodiment, the reaction mixture is extracted with an ether. In one embodiment, the ether is selected from diethyl ether, methyl ethyl ether, and methyl tert-butyl ether (MTBE). In one embodiment, the ether is MTBE.

In one embodiment, and after extraction, the reaction mixture is treated with an acid (e.g., HCl).

In one embodiment, the method of the present application further comprises hydrogenating Compound 4 to form Compound 5:

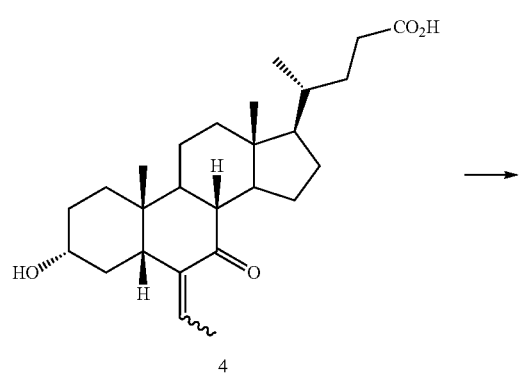

In one embodiment, the hydrogenation is conducted in the presence of a catalyst. In one embodiment, the catalyst is selected from a nickel catalyst (e.g., Raney nickel and Urushibara nickel), a palladium catalyst (e.g., Pd/C), and a platinum catalyst (e.g., PtO$_2$). In one embodiment, the catalyst is a palladium catalyst. In one embodiment, the catalyst is Pd/C.

In one embodiment, the reaction mixture is heated. In one embodiment, the reaction mixture is heated to about 80° C. to about 120° C., about 85° C. to about 110° C., about 90° C. to about 110° C., or about 95° C. to about 105° C.

In one embodiment, the method of the present application further comprises reducing the keto group at the C-7 position of Compound 5 to form OCA:

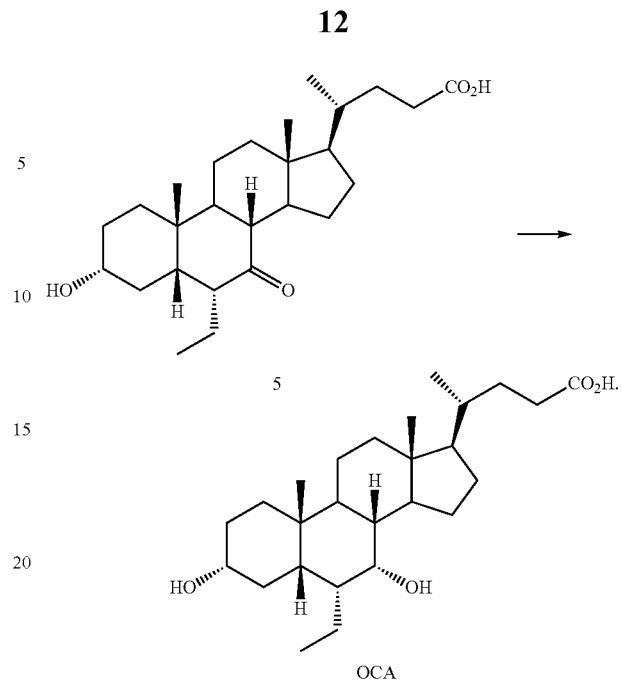

In one embodiment, the reduction comprises treating Compound 5 with a metal hydride. In one embodiment, the metal hydride is sodium borohydride or sodium triacetoxyborohydride.

In one embodiment, the present application provides a method of preparing OCA, or a pharmaceutical acceptable salt, solvate, or amino acid conjugate thereof, comprising a) reacting Compound 2 with paraldehyde to form Compound 3:

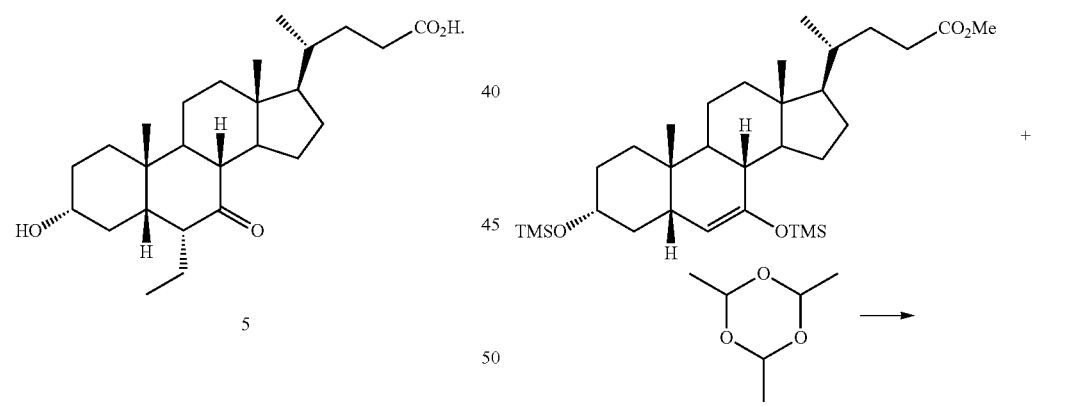

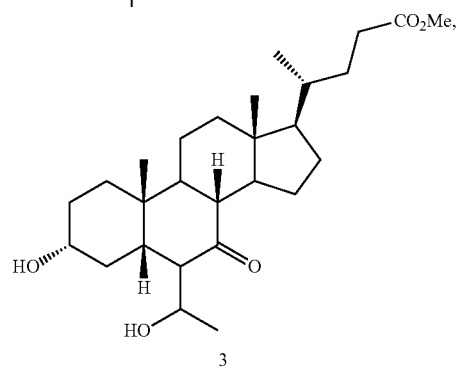

and b) reacting Compound 3 with a base to form Compound 4:

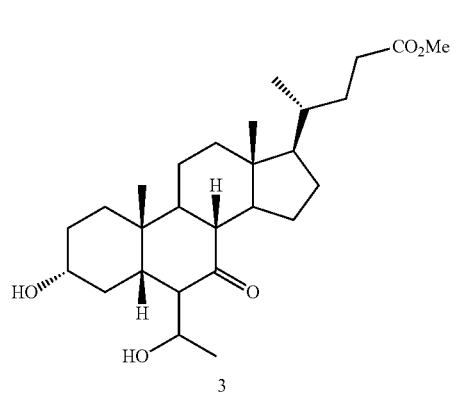
3 base ⟶

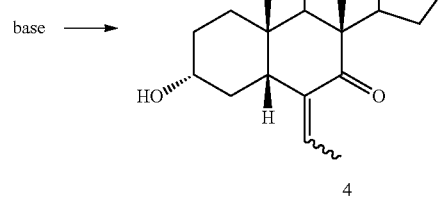
4

In one embodiment, step a) and step b) are each as described in detail above.

In one embodiment, the present application provides a method of preparing OCA, or a pharmaceutical acceptable salt, solvate, or amino acid conjugate thereof, comprising a) reacting Compound 2 with paraldehyde to form Compound 3:

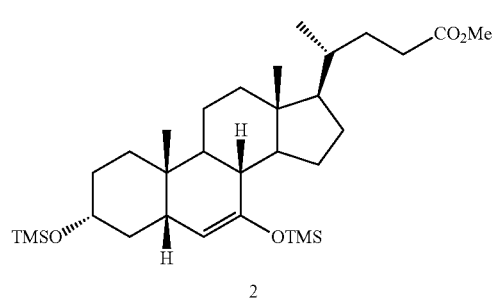
2

+

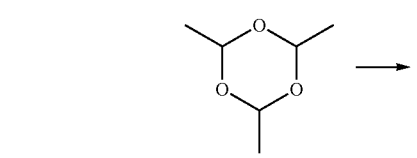

⟶

-continued

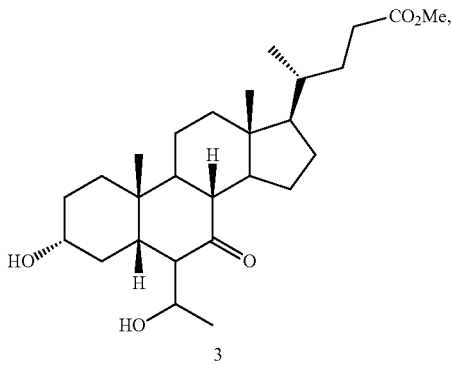
3 b) reacting Compound 3 with a base to form Compound 4:

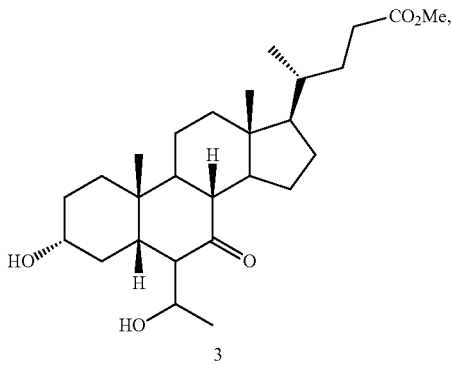
3

+ base ⟶

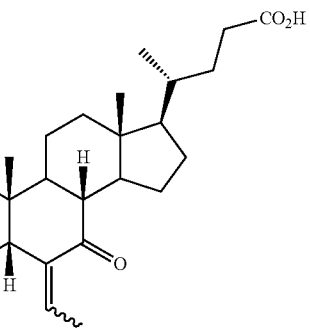
4 and c) hydrogenating Compound 4 to form Compound 5:

⟶

-continued

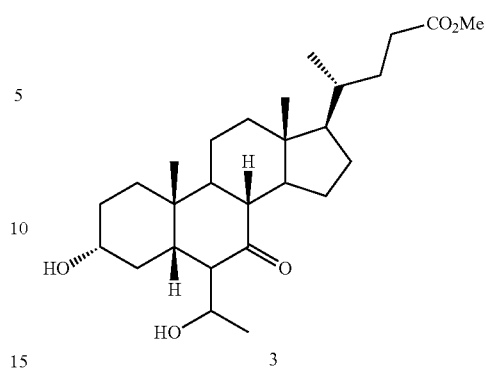

In one embodiment, step a), step b), and step c) are each as described in detail above.

In one embodiment, the present application provides a method of preparing OCA, or a pharmaceutical acceptable salt, solvate, or amino acid conjugate thereof, comprising a) reacting Compound 2 with paraldehyde to form Compound 3:

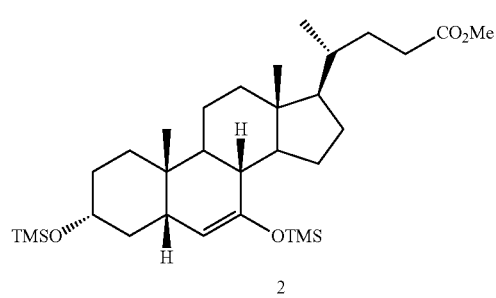

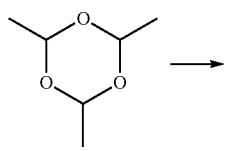

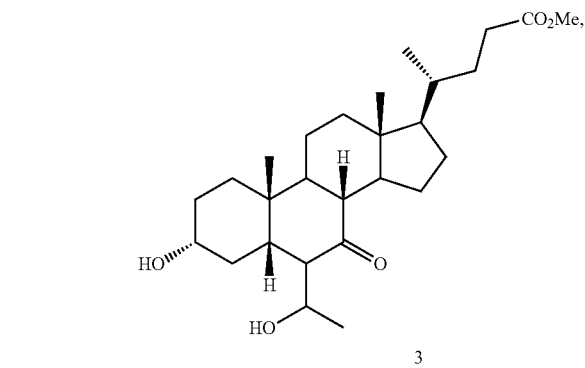

b) reacting Compound 3 with a base to form Compound 4:

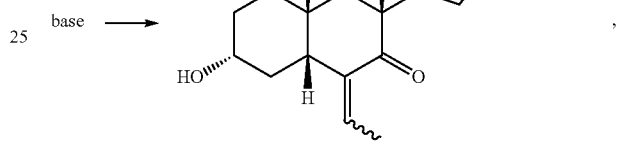

c) hydrogenating Compound 4 to form Compound 5:

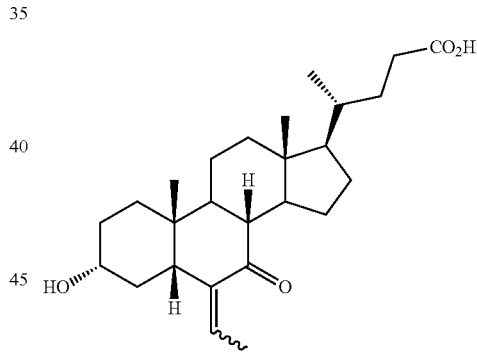

and d) reducing the keto group at the C-7 position of Compound 5 to form OCA:

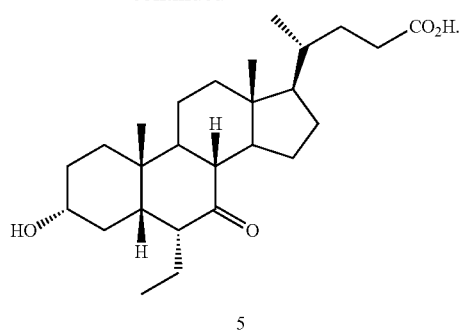

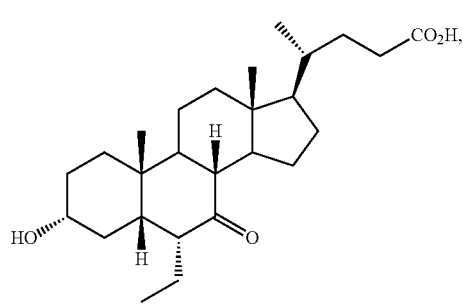

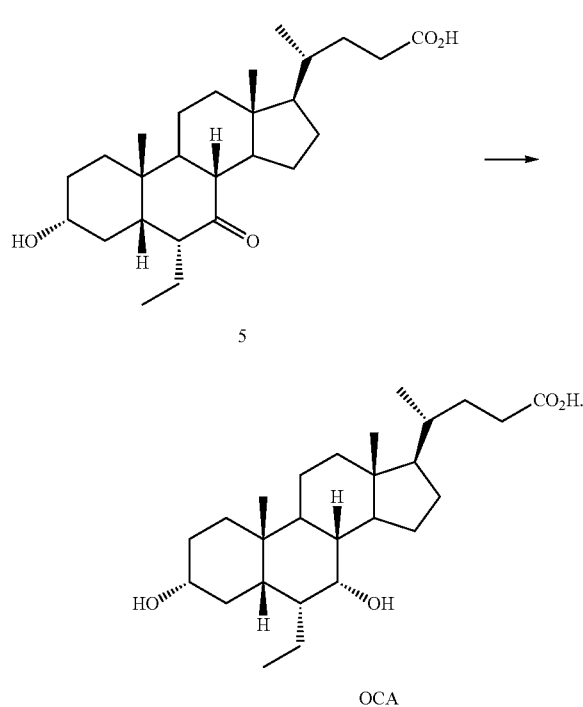

In one embodiment, step a), step b), step c), and step d) are each as described in detail above.

In one embodiment, the method of the present application further comprises reacting Compound 1 with tri-$C_1$-$C_3$ alkylsilyl halide to form Compound 2:

In one embodiment, the tri-$C_1$-$C_3$ alkylsilyl halide (e.g., tri-$C_1$-$C_3$ alkylsilyl bromide and tri-$C_1$-$C_3$ alkylsilyl chloride) is selected from trimethylsilyl halide, triethylsilyl halide, and tripropylsilyl halide. In one embodiment, the tri-$C_1$-$C_3$ alkylsilyl halide is trimethylsilyl chloride.

In one embodiment, the reaction is conducted in the presence of a strong base. In one embodiment, the strong base is selected from lithium diisopropylamide (LDA), lithium bis(trimethylsilyl)amide, sodium amide, and sodium hydride. In one embodiment, the strong base is LDA.

In one embodiment, the reaction is conducted in an aprotic solvent. In one embodiment, the aprotic solvent is a polar aprotic solvent. In one embodiment, the polar aprotic solvent is selected from tetrahydrofuran (THF), dimethylformamide (DMF), and dimethyl sulfoxide (DMSO). In one embodiment, the polar aprotic solvent is THF. In one embodiment, the aprotic solvent is a non-polar aprotic solvent. In one embodiment, the non-polar aprotic solvent is selected from toluene, hexane, heptane, benzene, 1,4-dioxane, chloroform, dichloromethane (DCM), diethyl ether, and methyl tert-butyl ether (MTBE). In one embodiment, the non-polar aprotic solvent is toluene.

In one embodiment, the reaction mixture is cooled. In one embodiment, the reaction mixture is cooled to about 0° C. to about −40° C., about −10° C. to about −40° C., about −10° C. to about −30° C., about −15° C. to about −30° C., about −20° C. to about −30° C., or about −20° C. to about −25° C.

In one embodiment, the method of the present application further comprises esterifying 7-keto lithocholic acid (KLCA) to form Compound 1:

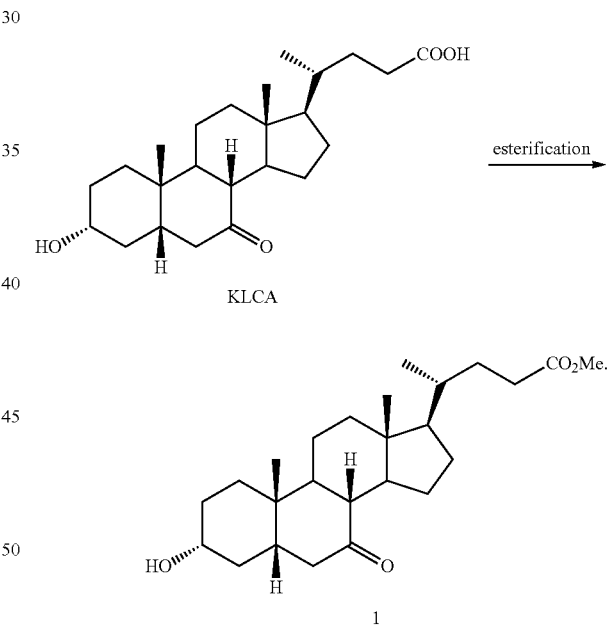

In one embodiment, the esterification is conducted at a temperature between about 30° C. and about 60° C.

In one embodiment, the esterification is conducted in the presence of an acid. In one embodiment, the acid is sulfuric acid or methanesulphonic acid.

In one embodiment, the present application provides a method of preparing OCA, or a pharmaceutical acceptable salt, solvate, or amino acid conjugate thereof, comprising a1) esterifying 7-keto lithocholic acid (KLCA) to form Compound 1:

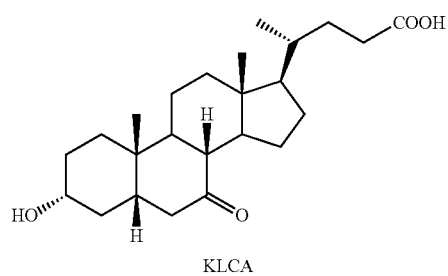

KLCA esterification →

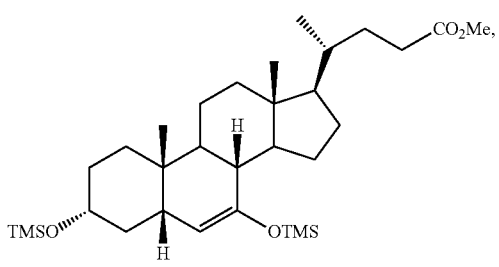

2

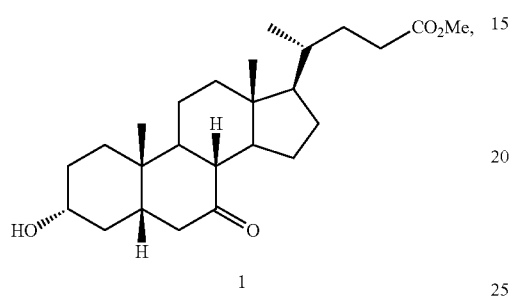

1 step a), as described above.

In one embodiment, the present application provides a method of preparing OCA, or a pharmaceutical acceptable salt, solvate, or amino acid conjugate thereof, comprising step a1), step a), and step b), each as described above. In one embodiment, the present application provides a method of preparing OCA, or a pharmaceutical acceptable salt, solvate, or amino acid conjugate thereof, comprising step a1), step a), step b), and step c), each as described above. In one embodiment, the present application provides a method of preparing OCA, or a pharmaceutical acceptable salt, solvate, or amino acid conjugate thereof, comprising step a1), step a), step b), step c), and step d) each as described above.

In one embodiment, the present application provides a method of preparing OCA, or a pharmaceutical acceptable salt, solvate, or amino acid conjugate thereof, comprising a2) reacting Compound 1 with tri-$C_1$-$C_3$ alkylsilyl halide to form Compound 2:

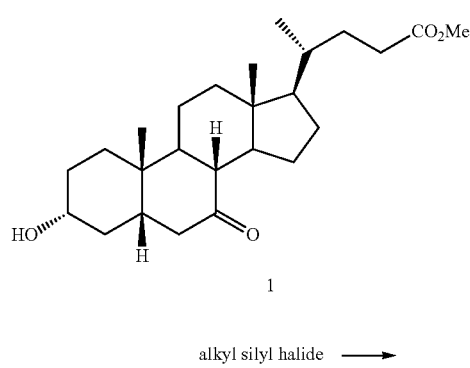

alkyl silyl halide → and step a), as described above.

In one embodiment, the present application provides a method of preparing OCA, or a pharmaceutical acceptable salt, solvate, or amino acid conjugate thereof, comprising step a1), step a2), and step a), each as described above. In one embodiment, the present application provides a method of preparing OCA, or a pharmaceutical acceptable salt, solvate, or amino acid conjugate thereof, comprising step a1), step a2), step a), and step b), each as described above. In one embodiment, the present application provides a method of preparing OCA, or a pharmaceutical acceptable salt, solvate, or amino acid conjugate thereof, comprising step a1), step a2), step a), step b), and step c), each as described above. In one embodiment, the present application provides a method of preparing OCA, or a pharmaceutical acceptable salt, solvate, or amino acid conjugate thereof, comprising step a1), step a2), step a), step b), step c), and step d) each as described above.

In one embodiment, the method of the present application is shown in the schemes below.

Scheme 1

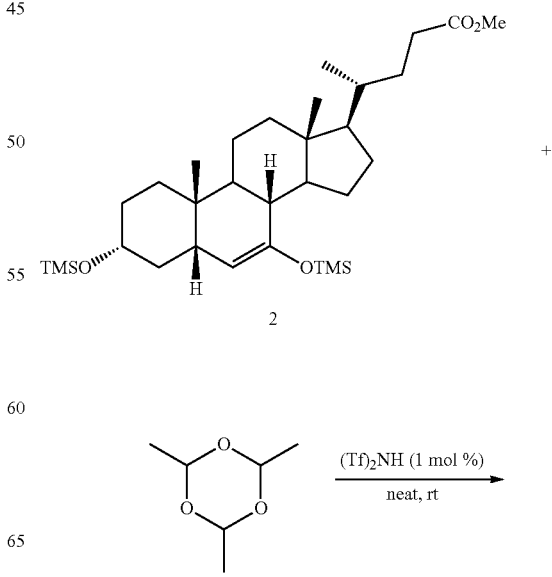

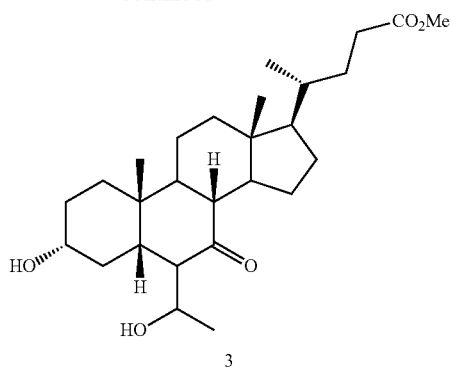

According to Scheme 1, Compound 2 can be dissolved in paraldehyde and added to (Tf)$_2$NH (e.g., catalytic amount) under an inert atmosphere (e.g., Ar). Compound 3 can be isolated in high yield (e.g. >85%).

Scheme 2

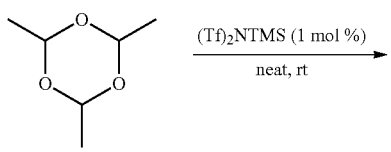

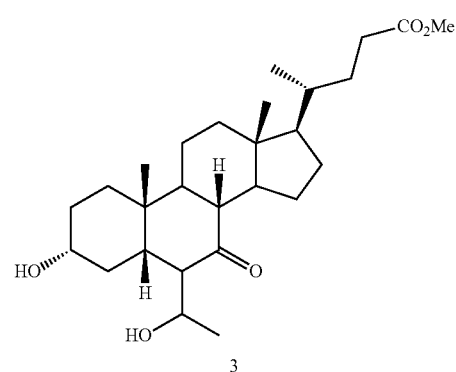

According to Scheme 2, Compound 2 can be dissolved in paraldehyde and TMS-triflimide (e.g., catalytic amount) can be added under an inert atmosphere (e.g., Ar).

Scheme 3

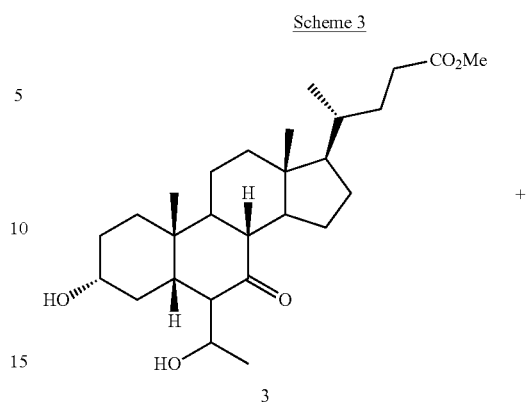

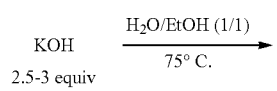

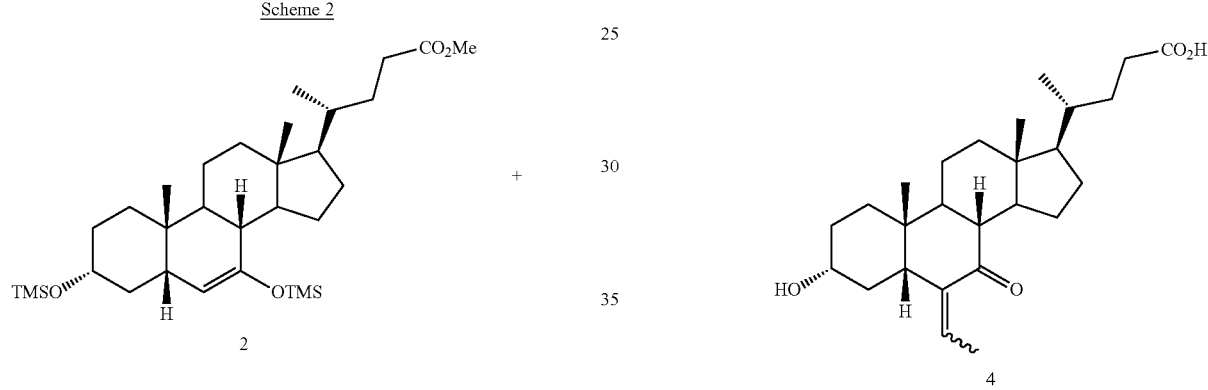

According to Scheme 3, Compound 3 can be dissolved in a mixture of solvents (e.g., EtOH and water (e.g., 1/1 v:v)), and a base (e.g., KOH) can be added. The resulting reaction mixture can be heated for a period of 1-10 h (e.g., 2 h).

The process of the present application is an improvement over the processes disclosed previously, e.g., as in WO2002/072598 and WO2006/122977, and more recently WO2013/192097. For example, WO2013/192097 describes a process for making OCA, comprising the steps shown in Scheme A below:

Scheme A

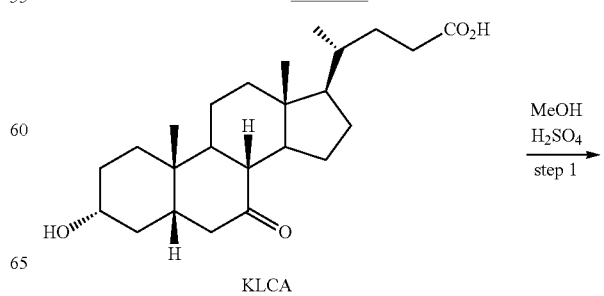

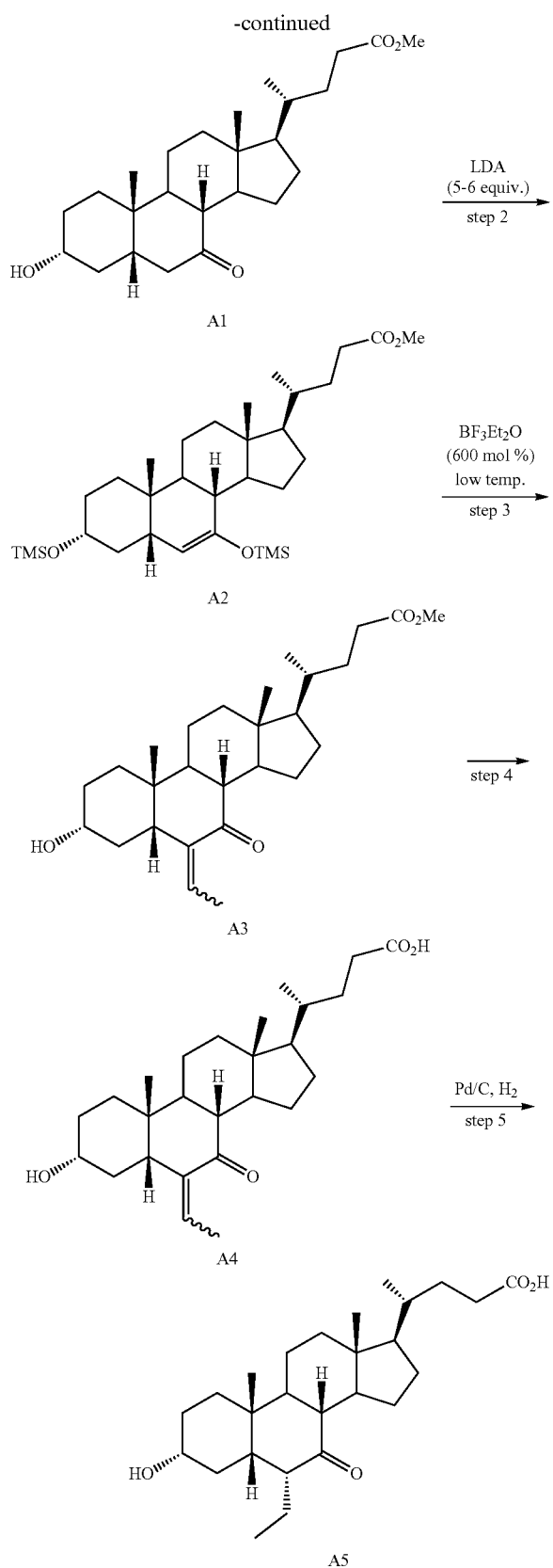

a methyl ester, Compound A1, by heating KLCA in methanol with sulfuric acid as the catalytic reagent. Compound A1 is isolated in 90-98% (e.g., 92%) yield. In Step 2, Compound A1 is treated with lithium di-isopropyl amide (LDA) in the presence of trimethylsilyl chloride (TMS-Cl) to generate Compound A2 having both a TMS-ether at the C-3 position and a silyl enol ether at the C-7 position. In step 3, Compound A2 is mixed with acetaldehyde and added to $BF_3$-$Et_2O$ at a low temperature to form Compound A3. In step 4, Compound A3 is subjected to hydrolysis (e.g., in NaOH aq.) to generate Compound A4.

In Scheme A, the synthesis of the silyl enol ether A2 requires a large excess of LDA and after work-up, the reaction generates a significant amount of diisopropyl amine as byproduct. In addition, a large excess of $BF_3.Et_2O$ is required to achieve significant conversion to A3, which is never isolated in pure form.

The method of the present application provides a number of improvements compared to previously described processes. Unexpectedly, changing the electrophile in the formation of the Mukaiyama aldol (i.e., Compound A3 in Scheme A and Compound 3 in the present application) from acetaldehyde (as in Scheme A) to paraldehyde (as in the present application) significantly improved the purity of Compound 4 and the overall yield of the synthesis.

In one embodiment, the method of the present application provides a substantially pure Compound 4:

In one embodiment, Compound 4 has a purity of greater than about 90%. In one embodiment, Compound 4 has a purity of greater than about 95%. For example, the purity of Compound 4 is about 95%, about 96%, about 97%, about 98%, about 99%, about 99.5%, about 99.8%, or about 99.9%. In one embodiment, the purity is determined by HPLC.

In one embodiment, the method of the present application provides an increased yield. In one embodiment, the method of the present application produces OCA, or a pharmaceutically acceptable salt, solvate, or amino acid conjugate thereof, at least 50%, at least 55%, at least 60%, at least 65%, at least 70%, at least 75%, at least 80%, at least 85%, at least 90%, or at least 95% yield. In one embodiment, the method of the present application produces OCA at least 65%, at least 70%, at least 75%, at least 80%, at least 85%, at least 90%, or at least 95% yield.

In one embodiment, the method of the present application produces substantially pure obeticholic acid, or a pharmaceutically acceptable salt, solvate, or amino acid conjugate thereof. The term "purity" as used herein refers to the amount of obeticholic acid based on analytic methods commonly used in the art (e.g., HPLC). Purity is based on the "organic" purity of the compound, and does not include a measure of any amount of water, solvent, metal, inorganic salt, etc. In one embodiment, the purity of obeticholic acid In Scheme A, Compound A5 is prepared through a 5-step synthetic process with the starting material 7-keto lithocholic acid (KLCA). In Step 1, KLCA is esterified to form is compared to the purity of the reference standard by comparing the area under the peak in HPLC. In one embodiment, the known standard for purity is an obeticholic acid reference standard. In one embodiment, obeticholic acid has a purity of greater than about 96%. In one embodiment, obeticholic acid has a purity of greater than about 98%. For example, the purity of obeticholic acid is 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.90%, 99.0%, 99.1%, 99.2%, 99.3%, 99.4%, 99.5%, 99.6%, 99.7%, 99.8%, or 99.9%. For example, the purity of obeticholic acid is 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, or 99.9%. For example, the purity of obeticholic acid is 98.0%, 98.5%, 99.0%, 99.5%, 99.6%, 99.7%, 99.8%, or 99.90%. For example, the purity of obeticholic acid is 98.5%, 99.0%, or 99.5%. In one embodiment, the purity is determined by HPLC.

In another embodiment, the purity of the obeticholic acid prepared by the method of the present application has a purity of 100% minus the amounts of water, sulphated ash, residual solvents, and other impurity contents such as 6-ethylursodeoxycholic acid, 3α-hydroxy-6α-ethyl-7-cheto-5β-cholan-24-oic acid, 6β-ethylchenodeoxycholic acid, 3α,7α-dihydroxy-6-ethyliden-5β-cholan-24-oic acid, chenodeoxycholic acid, and 3α(3α,7α-dihydroxy-6α-ethyl-5β-cholan-24-oyloxy)-7α-hydroxy-6α-ethyl-5β-cholan-24-oic acid.

In another embodiment, the purity of the obeticholic acid prepared by the method of the present application has a purity of 100% minus the amount of diisopropyl amine byproduct. In one embodiment, the obeticholic acid prepared according to the method of the present application contains less than about 10%, less than about 9%, less than about 8%, less than about 7%, less than about 6%, less than about 5%, less than about 4%, less than about 3%, less than about 2%, less than about 1%, less than about 0.5%, or less than about 0.1% diisopropyl amine byproduct.

In one embodiment, the obeticholic acid prepared according to the method of the present application contains less than about 10% of water, less than about 90% of water, less than 8% of water, less than 7% of water, less than 6% of water, less than 5% of water, less than 4% of water, less than 3% of water, less than 2% of water, or less than 1% of water.

In one embodiment, the obeticholic acid prepared according to the method of the present application contains not more than 0.15% of 6-ethylursodeoxycholic acid and 3α,7α-dihydroxy-6-ethyliden-5β-cholan-24-oic acid. In one embodiment, the obeticholic acid prepared according to the method of the present application contains less than about 0.07%, less than about 0.06%, or less than about 0.05% of 6-ethylursodeoxycholic acid and 3α,7α-dihydroxy-6-ethyliden-5β-cholan-24-oic acid.

In one embodiment, the obeticholic acid prepared according to the method of the present application contains not more than (NMT) 0.15% of 3α-hydroxy-6α-ethyl-7-cheto-5β-cholan-24-oic acid. In one embodiment, the obeticholic acid prepared according to the method of the present application contains less than about 0.07%, less than about 0.06%, or less than about 0.05% of 3α-hydroxy-6α-ethyl-7-cheto-5β-cholan-24-oic acid.

In one embodiment, the obeticholic acid prepared according to the method of the present application contains not more than (NMT) 0.15% of 6β-ethylchenodeoxycholic acid.

In one embodiment, the obeticholic acid prepared according to the method of the present application contains less than about 0.07%, less than about 0.06%, or less than about 0.05% of 6β-ethylchenodeoxycholic acid.

In one embodiment, the obeticholic acid prepared according to the method of the present application contains no more than (NMT) 3% of chenodeoxycholic acid (CDCA). In one embodiment, the obeticholic acid prepared according to the method of the present application contains less than about 1%, less than about 0.3%, or less than about 0.2% of CDCA.

In one embodiment, the obeticholic acid prepared according to the method of the present application contains no more than (NMT) 4% of CDCA and 6-ethylursodeoxycholic acid.

In one embodiment, the obeticholic acid prepared according to the method of the present application contains no more than (NMT) 1.5% of 3α(3α,7α-dihydroxy-6α-ethyl-5β-cholan-24-oyloxy)-7α-hydroxy-6α-ethyl-5β-cholan-24-oic acid. In one embodiment, the obeticholic acid prepared according to the method of the present application contains less than about 1%, less than about 0.07%, less than about 0.06%, or less than about 0.05% of 3α(3α,7α-dihydroxy-6α-ethyl-5β-cholan-24-oyloxy)-7α-hydroxy-6α-ethyl-5β-cholan-24-oic acid.

The present application provides methods for the synthesis of highly pure obeticholic acid which is safe and which produce obeticholic acid on a large scale. In one embodiment, obeticholic acid is produced on a commercial scale process. In one embodiment, the method of the present application produces obeticholic acid in high yield (>80%) and with limited impurities.

The present application also relates to a method of preparing 6α-ethyl-3α,7α-23-trihydroxy-24-nor-5β-cholan-23-sulfate (Compound 11):

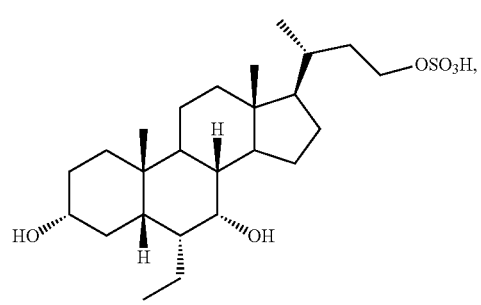

or a pharmaceutical acceptable salt, solvate, or amino acid conjugate thereof, comprising:

e) esterifying OCA to form Compound 6:

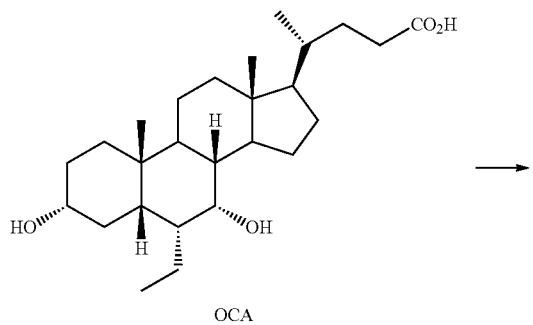

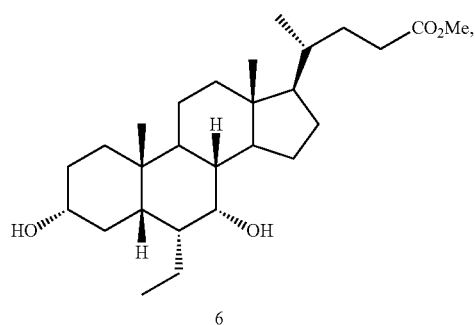
6
f) converting Compound 6 to form Compound 7:
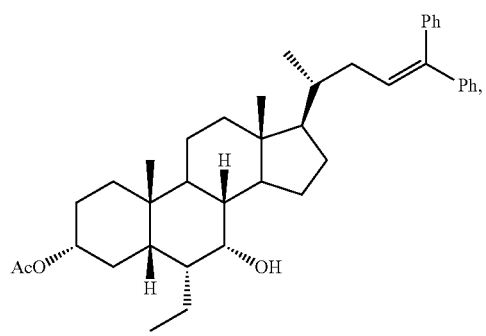
8
h) converting Compound 8 to form Compound 9:
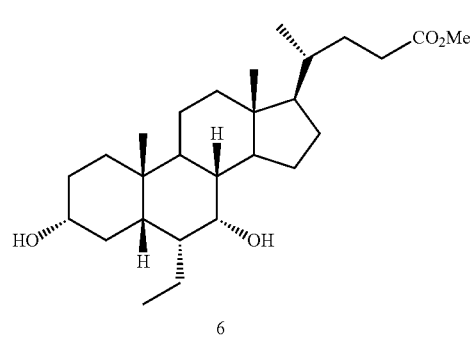
6
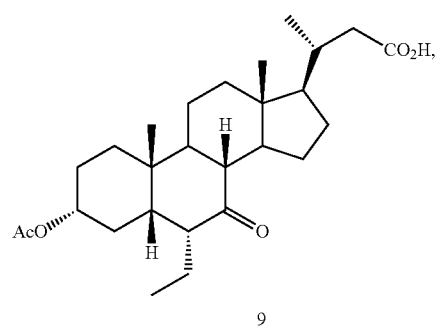
8
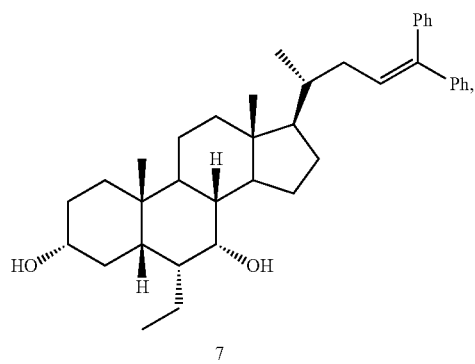
7
g) converting Compound 7 to form Compound 8:
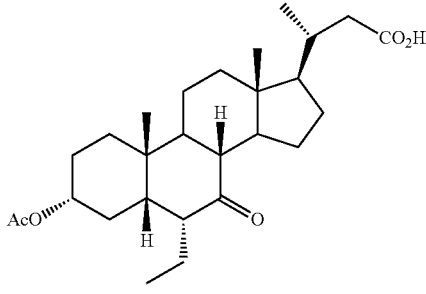
9
i) converting Compound 9 to form Compound 10:
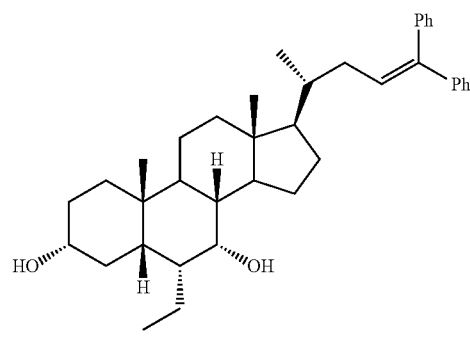
7

-continued

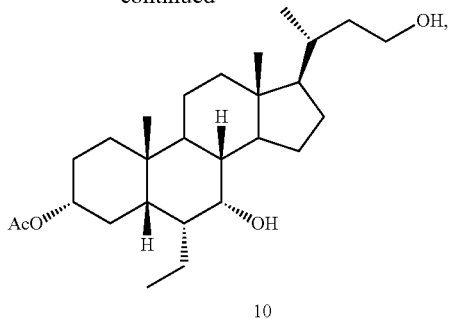
10 and
j) converting Compound 10 to form Compound 11:

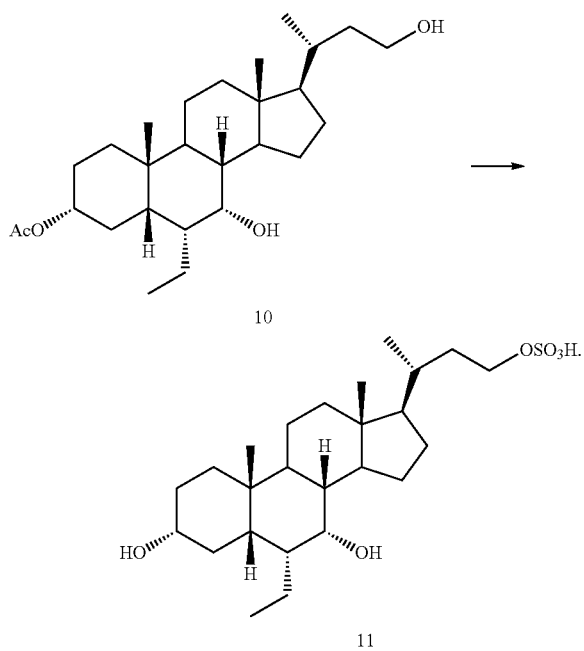

In one embodiment, the method further comprises preparing the sodium salt of Compound 11:

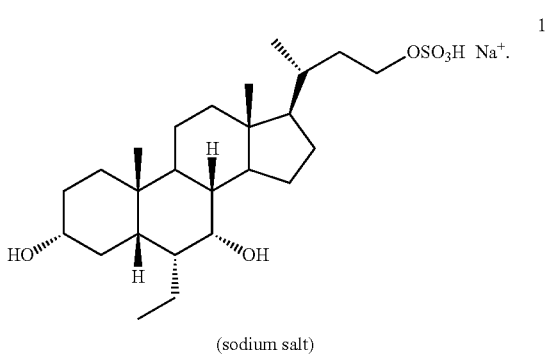
(sodium salt)

Step e) involves the esterification of OCA to form Compound 6. In one embodiment, the reaction is conducted in methanol. In another embodiment, the reaction is catalyzed with an acid. In one embodiment, the acid is p-toulenesulfonic acid. In one embodiment, the acid is sulfuric acid or methanesulphonic acid. In one embodiment, the esterification is performed at a temperature from about 55° C. to about 85° C., e.g., 55° C., 65° C., 75° C., and 85° C., as well as any temperature increment in between.

Step f) involves a Grignard reaction to afford Compound 7 via the formation of a diphenyl carbinol intermediate. In one embodiment, Compound 6 is first contacted with phenylmagnesium bromide to afford the diphenyl carbinol intermediate. In another embodiment, the molar ratio of phenylmagnesium bromide to Compound 6 is about 6:1. In another embodiment, the molar ratio of phenylmagnesium bromide to Compound 6 is about 5:1. In one embodiment, the reaction is performed in a non-protic solvent. In one embodiment, the non-protic is tetrahydrofuran. In one embodiment, an acid is added to the reaction after the formation of the diphenyl carbinol intermediate. In one embodiment, the acid is p-toluenesulfonic acid. In one embodiment, the reaction is performed at a temperature from about 50° C. to about 90° C., e.g., 50° C., 60° C., 70° C., 75° C., 80° C., and 90° C., as well as any temperature increment in between.

Step g) involves the protection of the hydroxyl group at the C-3 position of Compound 7 to afford Compound 8. In one embodiment, Compound 7 is contacted with acetic anhydride. In one embodiment, the molar ratio of acetic anhydride to Compound 7 is about 2:1. In another embodiment, the molar ratio is about 1.66. In one embodiment, the reaction is catalyzed by 4-dimethylaminopyridine (DMAP). In another embodiment, pyridine is added to the reaction. In another embodiment, the reaction is performed in diethyl ether or tetrahydrofuran. In one embodiment, the reaction is performed at a temperature below 30° C.

Step h) involves the oxidative cleavage of the double bond and the oxidation of the hydroxyl group at the C-7 position of Compound 8 to afford Compound 9. In one embodiment, Compound 8 is contacted with $RuCl_3$, $NaIO_4$, and an acid. In one embodiment, the molar ratio of Compound 8 to $RuCl_3$ is from about 18:1 to about 22:1. In one embodiment, the molar ratio of Compound 8 to $RuCl_3$ is from about 19:1 to about 21:1. In another embodiment, the molar ratio of Compound 8 to $RuCl_3$ is about 20:1. In one embodiment, the acid is selected from $H_2SO_4$, HCl, $HClO_4$, and $HIO_4$. In one embodiment, the acid is 2N $H_2SO_4$. In another embodiment, the acid is 2N HCl. In one embodiment, the molar ratio of Compound 8 to the acid is from about 2:1 to about 6:1. In one embodiment, the molar ratio of Compound 8 to the acid is from about 3:1 to about 5:1. In another embodiment, the molar of Compound 8 to the acid ratio is about 4:1. In one embodiment, the reaction is carried out at a temperature from about −10° C. to about 10° C. In another embodiment, the temperature is from about −5° C. to about 5° C. In another embodiment, the temperature is about 0° C. In one embodiment, the reaction is carried out in a mixture of solvents. In one embodiment, the mixture of solvents comprises one polar protic and two polar aprotic solvents. In one embodiment, the polar protic solvent is $H_2O$. In one embodiment, the polar aprotic solvents are acetonitrile and ethyl acetate. In one embodiment, the polar aprotic solvents are acetonitrile and chloroform. In one embodiment, the mixture of solvents is $H_2O$/ethyl acetate/acetonitrile. In one embodiment, the ratio of $H_2O$ to ethyl acetate to acetonitrile is from about 1:1:1 to about 1:3:2 by volume. In another embodiment, the ratio is about 1:1.5:1 to about 1:2.5:1.5 by volume. In another embodiment, the ratio is about 1:2:1.5 by volume.

Step i) involves the reduction of the C-23 carboxylic acid and C-7 carbonyl group of Compound 9 to afford Compound 10. In one embodiment, Compound 9 is contacted with a chloroformate, a base, and a reducing agent. In one embodiment, the chloroformate is isobutyl chloroformate, ethyl chloroformate, isopropyl chloroformate, or t-butyl chloroformate. In one embodiment, the chloroformate is isobutyl chloroformate. In one embodiment, the base is triethylamine. In one embodiment, the reducing agent is sodium borohydride or sodium triacetoxyborohydride. In one embodiment, the reaction is carried out in a polar aprotic solvent. In one embodiment, the polar aprotic solvent is tetrahydrofuran. In one embodiment, the reaction is carried out at a temperature from about −10° C. to about 10° C. In embodiment, the temperature is from about −5° C. to about 5° C. In another embodiment, the temperature is about 0° C.

Step j) involves the sulfation of the hydroxyl group at the C-23 position and deprotection of the hydroxyl group at the C-3 position of Compound 10 to afford Compound 11. In one embodiment, the sulfation is conducted with sulfur trioxide, chlorosulfonic acid, or sulphamic acid. In one embodiment, the sulfation is conducted with a sulfur trioxide complex. In one embodiment, the sulfur trioxide complex is selected from sulfur trioxide pyridine, sulfur trioxide dioxane, and sulfur trioxide trimethylamine. In one embodiment, the sulfur trioxide complex is sulfur trioxide pyridine.

In one embodiment, and the reaction mixture is treated with a base and a polar protic solvent to form the sodium salt of Compound 11. In one embodiment, the polar protic solvent is $CH_3OH$. In one embodiment, the base is NaOH. In one embodiment, the base is 10% (w/w) solution of NaOH in $CH_3OH$.

The present application further relates to a method of preparing a compound of Formula III as described in Scheme 4.

Scheme 4

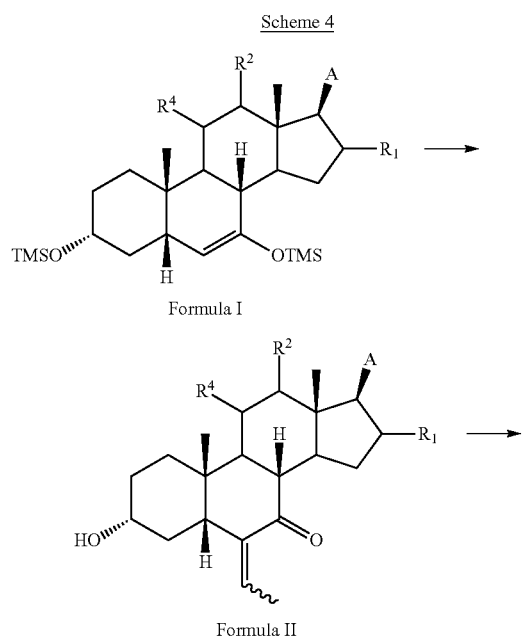

Formula I

Formula II

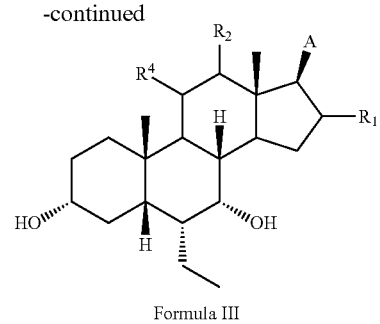

Formula III wherein:

A is

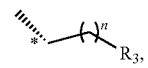

oxadiazolinyl, or isoxazolonyl, wherein the carbon atom marked with "*" is bonded to the carbon atom to which A is bonded;

n is 0, 1, or 2;

$R^1$, $R^2$, and $R^4$ are each independently H or OH;

$R^3$ is $(CR^5R^6)_pC(O)OH$, $(CR^5R^6)_pOH$, $(CR^5R^6)_pOSO_3H$; $(CR^5R^6)_pSO_3H$; $C(O)NHR^7$, tetrazolyl, oxadiazolyl, oxadiazolinyl, or thiazolidine-dionyl optionally substituted with $NHS(O)_2$—$(C_1-C_3)$ alkyl;

$R^5$ and $R^6$ are each independently H, halogen, OH, or alkyl optionally substituted with OH or halogen, $R^7$ is OH, $(CH_2)_pOH$, or $(CH_2)_pOSO_3H$;

p is 1 or 2; and wherein the hydroxyl groups of $R^1$, $R^2$, and $R^4$ may be protected.

In one embodiment, the compound of Formula III is selected from the group consisting of:

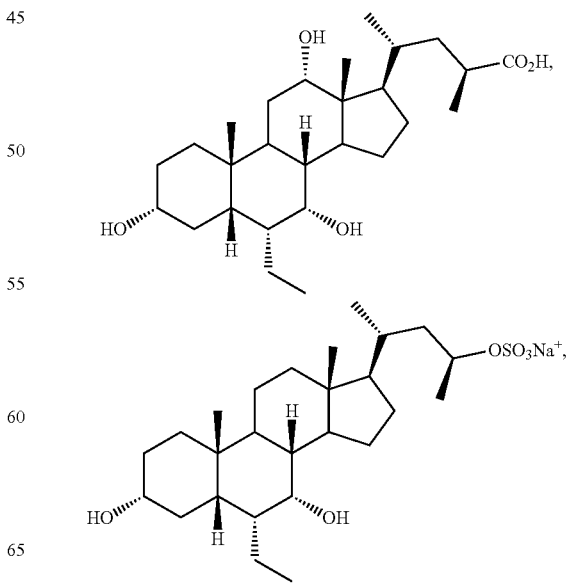

33
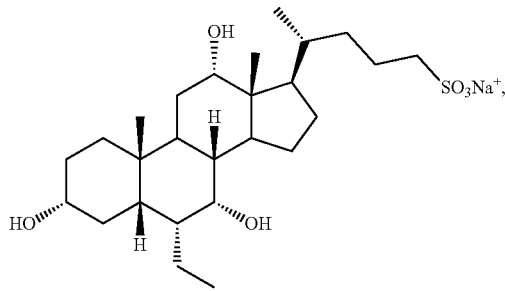
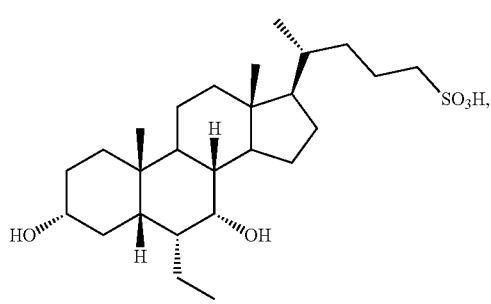
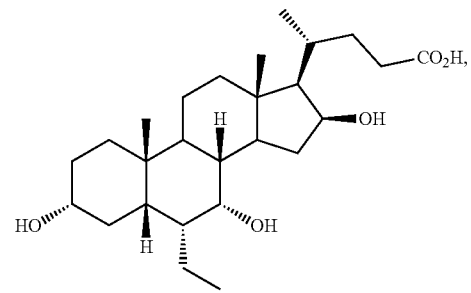
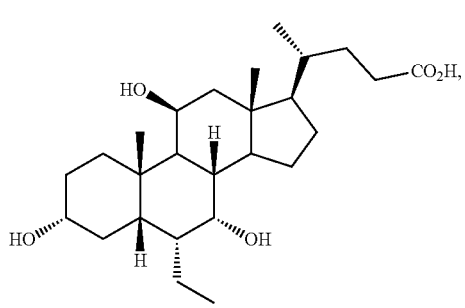
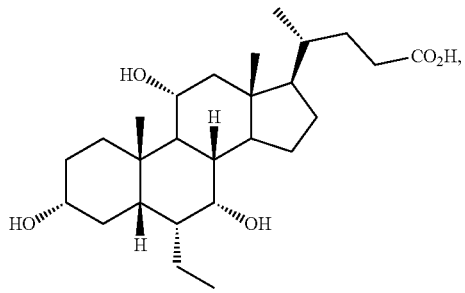
34
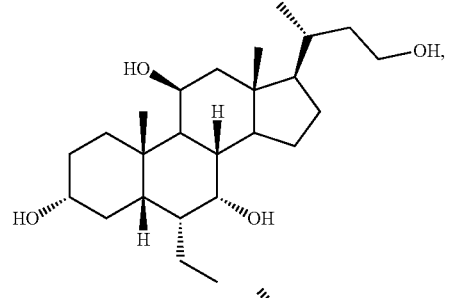
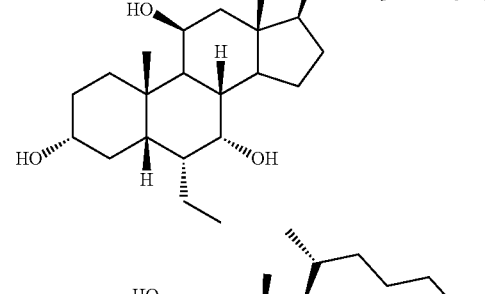
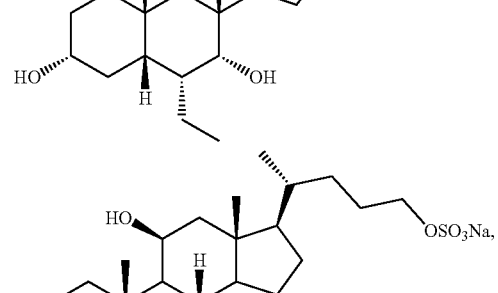
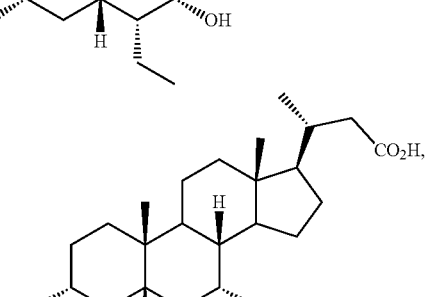
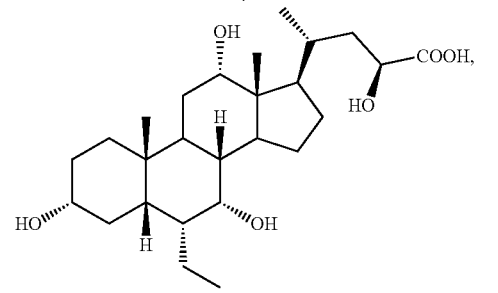

35
-continued
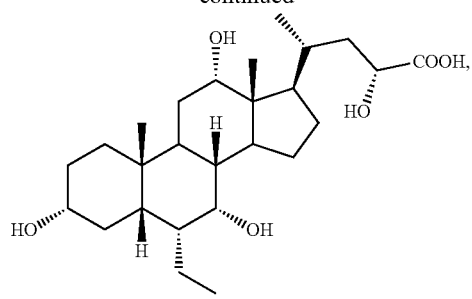
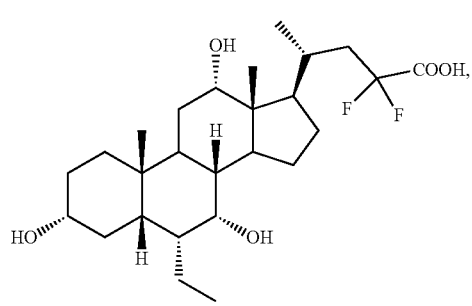
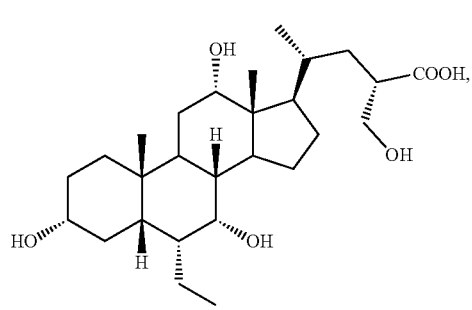
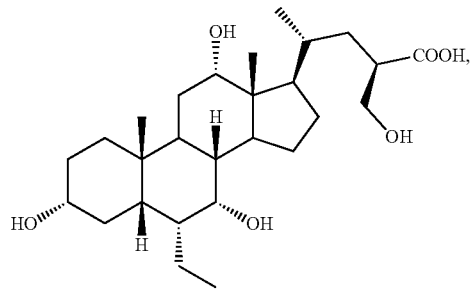
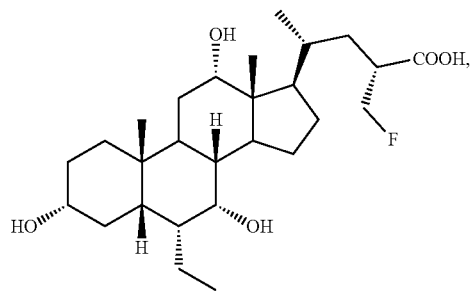
36
-continued
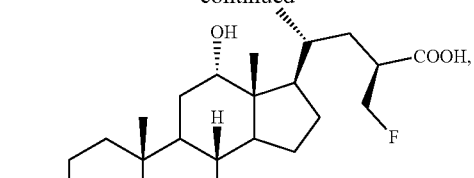
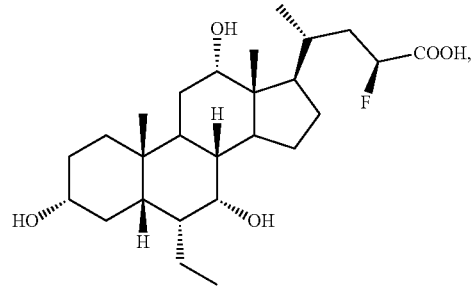
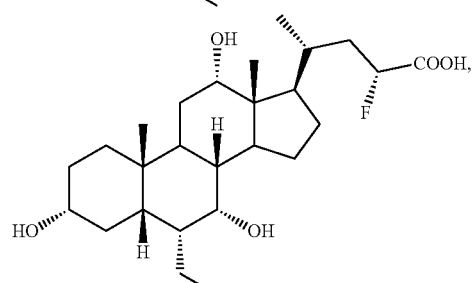
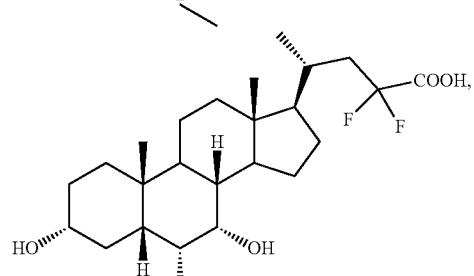
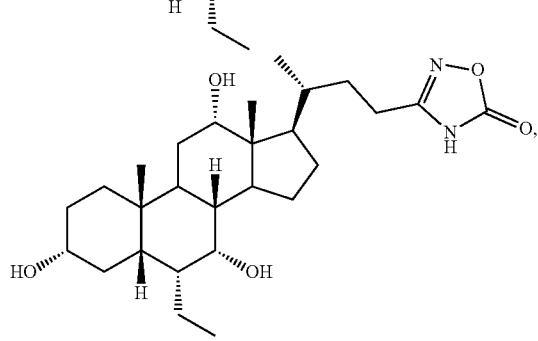
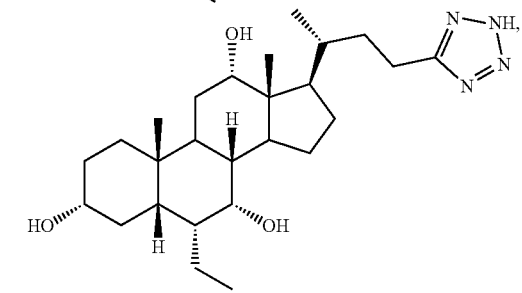

-continued
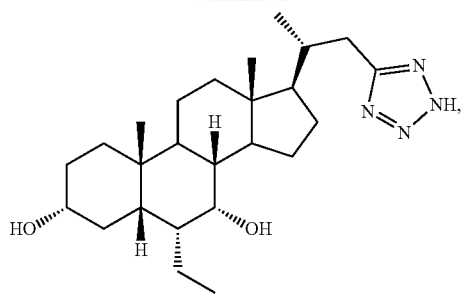
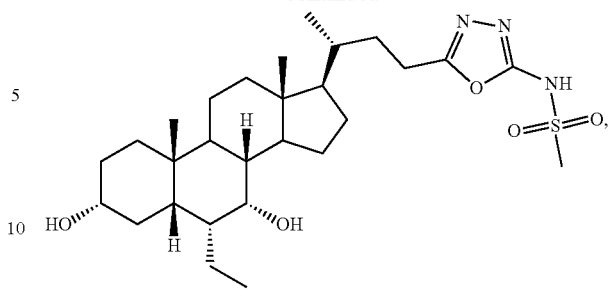
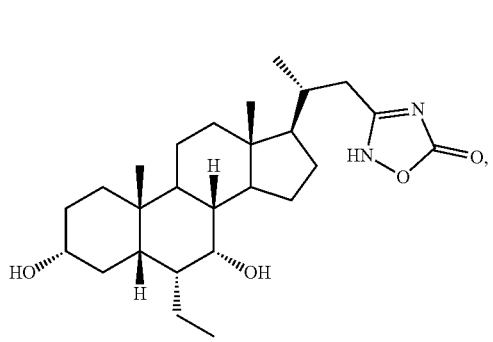
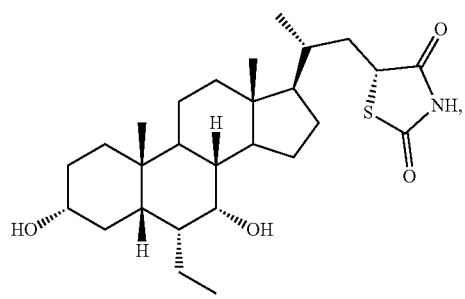
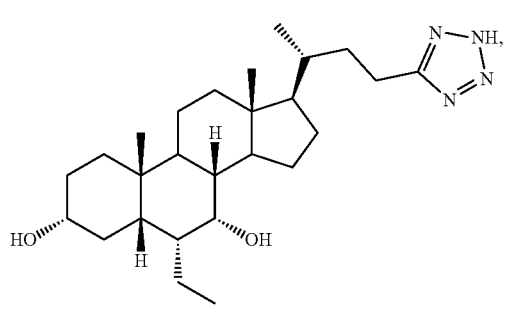
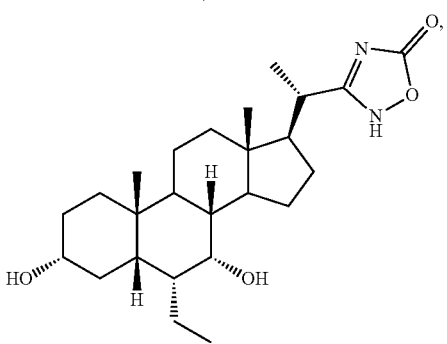
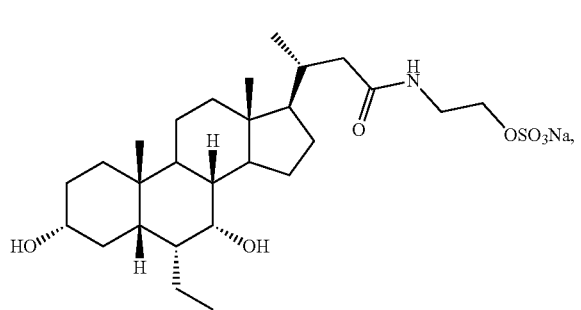
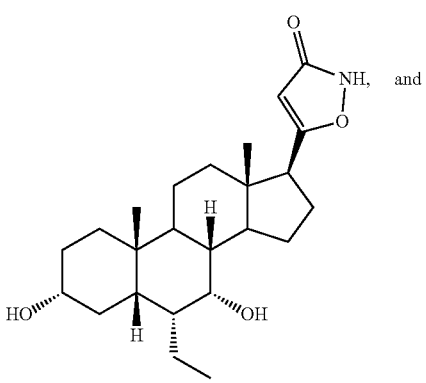
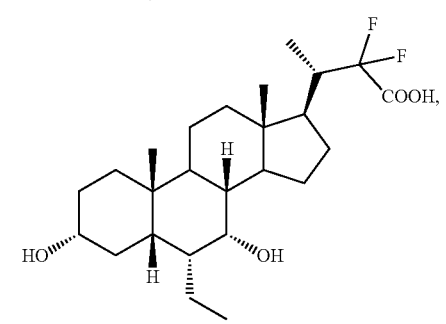
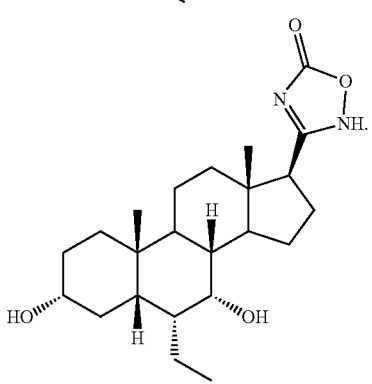

Oral Formulation and Administration

The present application provides a compound of the invention for oral administration. In one embodiment, the formulation relates to an oral administration for the prevention and treatment of FXR mediated diseases and conditions.

Formulations suitable for oral administration may be provided as discrete units, such as tablets, capsules, cachets (wafer capsule used by pharmacists for presenting a drug), lozenges, each containing a predetermined amount of a compound of the invention; as powders or granules; as solutions or suspensions in aqueous or non-aqueous liquids; or as oil-in-water or water-in-oil emulsions.

Formulations of the present application may be prepared by any suitable method, typically by uniformly and intimately admixing a compound of the invention with liquids or finely divided solid carriers or both, in the required proportions and then, if necessary, shaping the resulting mixture into the desired shape.

For example, a tablet may be prepared by compressing an intimate mixture comprising a powder or granules of a compound of the invention and one or more optional ingredients, such as a binder, lubricant, inert diluent, or surface active dispersing agent, or by molding an intimate mixture of powdered active ingredient and inert liquid diluent.

For example, one or more tablets may be administered to get to a target dose level based on the subject's weight, e.g., a human between about 30 kg to about 70 kg.

In addition to the ingredients specifically mentioned above, the oral formulations of the present application may include other agents known to those skilled in the art of pharmacy, having regard for the type of formulation in issue. Oral formulations may include suitable flavoring agents.

In one embodiment, the present application relates to a pharmaceutical formulation of a compound of the invention, wherein the compound of the invention is produced by a process of the application. In another embodiment, the formulation is administered orally.

In one embodiment, the formulation is in tablet form. In another embodiment, the formulation comprises a compound of the invention and one or more components selected from microcrystalline cellulose, sodium starch glycolate, magnesium stearate, coating material, and colloidal silicon dioxide. In one embodiment, the coating material is an Opadry® coating material.

All percentages and ratios used herein, unless otherwise indicated, are by weight or molar equivalents. The percent dimeric impurity is calculated on an area percent basis, typically as quantified by analytical HPLC.

Pharmaceutical Compositions

A compound of the invention is useful for a variety of medicinal purposes. A compound of the invention may be used in methods for the prevention or treatment of FXR mediated diseases and conditions. In one embodiment, the disease or condition is selected from biliary atresia, cholestatic liver disease, chronic liver disease, nonalcoholic steatohepatitis (NASH), hepatitis C infection, alcoholic liver disease, primary biliary cirrhosis (PBC), liver damage due to progressive fibrosis, liver fibrosis, and cardiovascular diseases including atherosclerosis, arteriosclerosis, hypercholesteremia, and hyperlipidemia. In one embodiment, a compound of the invention may be used in methods for lowering triglycerides and/or increasing HDL. Other effects of a compound of the invention include lowering alkaline phosphatase (ALP), bilirubin, ALT, AST, and GGT. In one embodiment, the present application relates to a pharmaceutical composition comprising a compound of the invention and a pharmaceutically acceptable carrier, wherein the compound of the invention is produced by a method of the present application.

In one embodiment, the compound or pharmaceutical composition is administered orally, parenterally, or topically. In one embodiment, the compound or pharmaceutical composition is administered orally.

In one embodiment, the present application relates to a method for inhibiting fibrosis in a subject who is suffering from a cholestatic condition, the method comprising the step of administering to the subject an effective amount of a compound of the invention, wherein the compound of the invention is produced by the method of the present application. In one embodiment, the present application relates to a method for inhibiting fibrosis in a subject who is not suffering from a cholestatic condition, the method comprising the step of administering to the subject an effective amount of a compound of the invention, wherein the compound of the invention is produced by the method of the present application. In one embodiment, the fibrosis to be inhibited occurs in an organ where FXR is expressed.

In one embodiment, the cholestatic condition is defined as having abnormally elevated serum levels of alkaline phosphatase, 7-glutamyl transpeptidase (GGT), and 5' nucleotidase. In another embodiment, the cholestatic condition is further defined as presenting with at least one clinical symptom. In another embodiment, the symptom is itching (pruritus). In another embodiment, the fibrosis is selected from the group consisting of liver fibrosis, kidney fibrosis, and intestinal fibrosis. In another embodiment, the cholestatic condition is selected from the group consisting of primary biliary cirrhosis, primary sclerosing cholangitis, drug-induced cholestasis, hereditary cholestasis, and intrahepatic cholestasis of pregnancy. In another embodiment, the subject is not suffering from a cholestatic condition associated with a disease or condition selected from the group consisting of primary liver and biliary cancer, metastatic cancer, sepsis, chronic total parenteral nutrition, cystic fibrosis, and granulomatous liver disease.

In one embodiment, the subject has liver fibrosis associated with a disease selected from the group consisting of hepatitis B; hepatitis C; parasitic liver diseases; post-transplant bacterial, viral and fungal infections; alcoholic liver disease (ALD); non-alcoholic fatty liver disease (NAFLD); non-alcoholic steatohepatitis (NASH); liver diseases induced by methotrexate, isoniazid, oxyphenistatin, methyldopa, chlorpromazine, tolbutamide, or amiodarone; autoimmune hepatitis; sarcoidosis; Wilson's disease; hemochromatosis; Gaucher's disease; types III, IV, VI, IX and X glycogen storage diseases; $\alpha_1$-antitrypsin deficiency; Zellweger syndrome; tyrosinemia; fructosemia; galactosemia; vascular derangement associated with Budd-Chiari syndrome, veno-occlusive disease, or portal vein thrombosis; and congenital hepatic fibrosis.

In one embodiment, the subject has intestinal fibrosis associated with a disease selected from the group consisting of Crohn's disease, ulcerative colitis, post-radiation colitis, and microscopic colitis.

In one embodiment, the subject has renal fibrosis associated with a disease selected from the group consisting of diabetic nephropathy, hypertensive nephrosclerosis, chronic glomerulonephritis, chronic transplant glomerulopathy, chronic interstitial nephritis, and polycystic kidney disease.

Definitions

As used herein, a "compound of the invention" refers to obeticholic acid (OCA), 6α-ethyl-3α,7α-23-trihydroxy-24-nor-5β-cholan-23-sulfate (Compound 11), their described derivatives, such as, for example, compounds of Formula III, and reaction intermediates, such as, for example, Compound 3, or a pharmaceutically acceptable salt, solvate, or amino acid conjugate thereof.

"Treating", includes any effect, e.g., lessening, reducing, modulating, or eliminating, that results in the improvement of the condition, disease, disorder, etc. "Treating" or "treatment" of a disease state includes inhibiting the disease state, i.e., arresting the development of the disease state or its clinical symptoms; or relieving the disease state, i.e., causing temporary or permanent regression of the disease state or its clinical symptoms.

"Preventing" the disease state includes causing the clinical symptoms of the disease state not to develop in a subject that may be exposed to or predisposed to the disease state, but does not yet experience or display symptoms of the disease state.

"Disease state" means any disease, disorder, condition, symptom, or indication.

As used herein, the term "about" or "approximately", or the like, when used together with a numeric value, may include a range of numeric values which is more or less than the numeric value to which the term refers or relate. For example, the range can include numeric values that are from 10% less to 10% more, from 9% less to 9%, more, from 8% less to 8% more, from 7% less to 7% more, from 6% less to 6% more, from 5% less to 5% more, from 4% less to 4% more, from 3% less to 3% more, from 2% less to 2% more, or from 1% less to 1% more, than the numeric value to which the term refers or relate. For example, "about 5" can include numeric values from 4.5 to 5.5, from 4.55 to 5.45, from 4.6 to 5.4, from 4.65 to 5.35, from 4.7 to 5.3, from 4.75 to 5.25, from 4.8 to 5.2, from 4.85 to 5.15, from 4.9 to 5.1, or from 4.95 to 5.05.

The term "effective amount" as used herein refers to an amount of a compound of the invention (e.g., an FXR-activating ligand) that produces an acute or chronic therapeutic effect upon appropriate dose administration. The effect includes the prevention, correction, inhibition, or reversal of the symptoms, signs and underlying pathology of a disease/condition (e.g., fibrosis of the liver, kidney, or intestine) and related complications to any detectable extent.

"A therapeutically effective amount" means the amount of a compound of the invention that, when administered to a mammal for treating a disease, is sufficient to effect such treatment for the disease. The "therapeutically effective amount" will vary depending on the disease and its severity and the age, weight, etc., of the mammal to be treated.

A therapeutically effective amount of a compound of the invention can be formulated with a pharmaceutically acceptable carrier for administration to a human or an animal. Accordingly, a compound of the invention or its formulations can be administered, for example, via oral, parenteral, or topical routes, to provide an effective amount of the compound. In alternative embodiments, a compound of the invention prepared in accordance with the present application can be used to coat or impregnate a medical device, e.g., a stent.

The application also comprehends isotopically-labeled compound of the invention, or pharmaceutically acceptable salts, solvate, or amino acid conjugates thereof, which are identical to those recited in the application and following, but for the fact that one or more atoms are replaced by an atom having an atomic mass or mass number different from the atomic mass or mass number most commonly found in nature. Examples of isotopes that can be incorporated into a compound of the invention include isotopes of hydrogen, carbon, nitrogen, fluorine, such as $^{3}H$, $^{11}C$, $^{13}C$, $^{14}C$ and $^{18}F$.

Tritiated, i.e., $^{3}H$, carbon-13, i.e., $^{13}C$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example, increased in-vivo half-life or reduced dosage requirements and, hence, may be preferred in some circumstances. Isotopically labeled compounds of the invention can generally be prepared by carrying out the procedures disclosed in the Schemes and/or in the Examples of the application, by substituting a readily available isotopically labeled reagent for a non-isotopically labeled reagent. In one embodiment, a compound of the invention is not isotopically labelled. In one embodiment, a deuterated compound of the invention is useful for bioanalytical assays. In another embodiment, a compound of the invention is radiolabelled.

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

"Solvates" means solvent addition forms that contain either stoichiometric or non stoichiometric amounts of solvent. A compound of the invention may have a tendency to trap a fixed molar ratio of solvent molecules in the crystalline solid state, thus forming a solvate. If the solvent is water, the solvate formed is a hydrate. When the solvent is alcohol, the solvate formed is an alcoholate. Hydrates are formed by the combination of one or more molecules of water with one of the substances in which the water retains its molecular state as $H_2O$, such combination being able to form one or more hydrates. Additionally, compounds of the present application, for example, the salts of the compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc.

"Tautomers" refers to compounds whose structures differ markedly in the arrangement of atoms, but which exist in rapid equilibrium. It is to be understood that a compound of the invention may be depicted as different tautomers. It should also be understood that when a compound of the invention and synthetic intermediates of the application have tautomeric forms, all tautomeric forms are intended to be within the scope of the application, and the naming of the compound of the invention does not exclude any tautomer form. A compound of the invention and synthetic intermediates of the application can exist in several tautomeric forms, including the keto-enol. For example, in keto-enol tautomerism a simultaneous shift of electrons and a hydrogen atom occurs. Tautomers exist as mixtures of a tautomeric set in solution. In solid form, usually one tautomer predominates. Even though one tautomer may be described, the present application includes all tautomers of the present compounds.

A "pharmaceutical composition" is a formulation containing a compound of the invention in a form suitable for administration to a subject. In one embodiment, the pharmaceutical composition is in bulk or in unit dosage form. It can be advantageous to formulate compositions in dosage unit form for ease of administration and uniformity of dosage. Dosage unit form, as used herein, refers to physically discrete units suited as unitary dosages for the subject to be treated; each unit containing a predetermined quantity of active reagent calculated to produce the desired therapeutic effect in association with the required pharmaceutical carrier. The specification for the dosage unit forms of the application are dictated by and directly dependent on the unique characteristics of the active reagent and the particular therapeutic effect to be achieved, and the limitations inherent in the art of compounding such an active agent for the treatment of individuals.

The unit dosage form is any of a variety of forms, including, for example, a capsule, an IV bag, a tablet, a single pump on an aerosol inhaler, or a vial. The quantity of a compound of the invention (e.g., a formulation of a compound of the invention, or a pharmaceutically acceptable salt, solvate, or amino acid conjugate thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this application include powders, sprays, ointments, pastes, creams, lotions, gels, solutions, patches and inhalants. In one embodiment, a compound of the invention is mixed under sterile conditions with a pharmaceutically acceptable carrier, and with any preservatives, buffers, or propellants that are required.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In one embodiment, the subject is human. In one embodiment, the subject is human child (e.g., between about 30 kg to about 70 kg). In one embodiment, the human child has had a Kasai procedure, where the Kasai procedure effectively gives them a functional bile duct when they are born either without a bile duct or it is completely blocked at birth.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

While it is possible to administer a compound of the invention directly without any formulation, the compound of the invention is usually administered in the form of pharmaceutical formulations comprising a pharmaceutically acceptable excipient and the compound of the invention. These formulations can be administered by a variety of routes including oral, buccal, rectal, intranasal, transdermal, subcutaneous, intravenous, intramuscular, and intranasal. Oral formulations of a compound of the invention are described further herein under the section entitled "Oral Formulation and Administration".

In one embodiment, a compound of the invention can be administered transdermally. In order to administer transdermally, a transdermal delivery device ("patch") may be needed. Such transdermal patches may be used to provide continuous or discontinuous infusion of a compound of the present application in controlled amounts. The construction and use of transdermal patches for the delivery of pharmaceutical agents is well known in the art. See, e.g., U.S. Pat. No. 5,023,252. Such patches may be constructed for continuous, pulsatile, or on demand delivery of pharmaceutical agents.

"Fibrosis" refers to a condition involving the development of excessive fibrous connective tissue, e.g., scar tissue, in a tissue or organ. Such generation of scar tissue may occur in response to infection, inflammation, or injury of the organ due to a disease, trauma, chemical toxicity, and so on. Fibrosis may develop in a variety of different tissues and organs, including the liver, kidney, intestine, lung, heart, etc.

The term "inhibiting" or "inhibition," as used herein, refers to any detectable positive effect on the development or progression of a disease or condition. Such a positive effect may include the delay or prevention of the onset of at least one symptom or sign of the disease or condition, alleviation or reversal of the symptom(s) or sign(s), and slowing or prevention of the further worsening of the symptom(s) or sign(s).

As used herein, a "cholestatic condition" refers to any disease or condition in which bile excretion from the liver is impaired or blocked, which can occur either in the liver or in the bile ducts. Intrahepatic cholestasis and extrahepatic cholestasis are the two types of cholestatic conditions. Intrahepatic cholestasis (which occurs inside the liver) is most commonly seen in primary biliary cirrhosis, primary sclerosing cholangitis, sepsis (generalized infection), acute alcoholic hepatitis, drug toxicity, total parenteral nutrition (being fed intravenously), malignancy, cystic fibrosis, and pregnancy. Extrahepatic cholestasis (which occurs outside the liver) can be caused by bile duct tumors, strictures, cysts, diverticula, stone formation in the common bile duct, pancreatitis, pancreatic tumor or pseudocyst, and compression due to a mass or tumor in a nearby organ.

Clinical symptoms and signs of a cholestatic condition include itching (pruritus), fatigue, jaundiced skin or eyes, inability to digest certain foods, nausea, vomiting, pale stools, dark urine, and right upper quadrant abdominal pain. A patient with a cholestatic condition can be diagnosed and followed clinically based on a set of standard clinical laboratory tests, including measurement of levels of alkaline phosphatase, γ-glutamyl transpeptidase (GGT), 5' nucleotidase, bilirubin, bile acids, and cholesterol in a patient's blood serum. Generally, a patient is diagnosed as having a cholestatic condition if serum levels of all three of the diagnostic markers alkaline phosphatase, GGT, and 5' nucleotidase, are considered abnormally elevated. The normal serum level of these markers may vary to some degree from laboratory to laboratory and from procedure to procedure, depending on the testing protocol. Thus, a physician will be able to determine, based on the specific laboratory and test procedure, what is an abnormally elevated blood level for each of the markers. For example, a patient suffering from a cholestatic condition generally has greater than about 125 IU/L alkaline phosphatase, greater than about 65 IU/L GGT, and greater than about 17 NIL 5' nucleotidase in the blood. Because of the variability in the level of serum markers, a cholestatic condition may be diagnosed on the basis of abnormal levels of these three markers in addition to at least one of the symptoms mentioned above, such as itching (pruritus).

The term "organ" refers to a differentiated structure (as in a heart, lung, kidney, liver, etc.) consisting of cells and tissues and performing some specific function in an organism. This term also encompasses bodily parts performing a function or cooperating in an activity (e.g., an eye and related structures that make up the visual organs). The term "organ" further encompasses any partial structure of differentiated cells and tissues that is potentially capable of developing into a complete structure (e.g., a lobe or a section of a liver).

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The application having now been described by way of written description, those of skill in the art will recognize that the application can be practiced in a variety of embodiments and that the foregoing description and examples below are for purposes of illustration and not limitation of the claims that follow.

In the specification, the singular forms also include the plural, unless the context clearly dictates otherwise. Unless defined otherwise, all technical and scientific terms used herein have the same meaning as commonly understood by one of ordinary skill in the art to which this application belongs. In the case of conflict, the present specification will control.

EXAMPLES

Example 1: Purification of Compound 2

Crude Compound 2 (10 g) was purified over a short plug silica gel (20.0 g) column chromatography using 10% EtOAc in hexanes.

Alternatively, Compound 2 (41.0 g) was purified over a short plug silica gel (80.0 g) column chromatography using 10% EtOAc in hexanes (5 fractions of 100 ml were collected). After all the solvent was removed, 34.3 g of Compound 2 was obtained as a yellow oil.

Alternatively, Compound 2 was dissolved in THF and dried over $MgSO_4$. The solvent was removed and the compound was dried under high vacuum (1×10-2 mbar) for 30 min.

Alternatively, Compound 2 (6.7 g) was dissolved in 12 ml of PhMe, and $MgSO_4$ (6.7 g) was added. The mixture was stirred at room temperature for 30 min, filtered to remove $MgSO_4$, and washed with PhMe (10 ml×2). The solvent was removed and 5.5 g of Compound 2 was obtained.

Example 2: Preparation of Compound 3

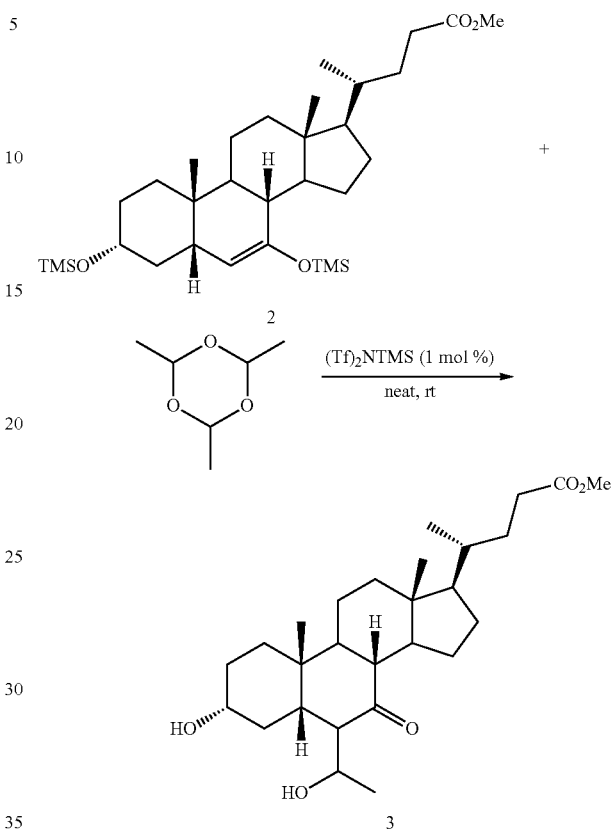

Compound 2 (4.27 g, 8 mmol) is dissolved in paraldehyde (4 equiv, 32.0 mmol, 4.0 mL) and added to a flask containing 1 mol % of $(Tf)_2NH$ (22.5 mg, 0.08 mmol) under an atmosphere of Ar. After a 30 min period of stirring, during which Compound 3 is precipitated as a colorless solid, the reaction mixture is diluted with water, filtered and washed with water. Compound 3 is isolated with >85% yield.

Alternatively, Compound 2 (1.376 g, 2.57 mmol) is dissolved in paraldehyde (4 equiv, 10.28 mmol, 1.25 mL), and 1 mol % of TMS-triflimide (0.0257 mmol, 12 µL) is added under an atmosphere of Ar. After a 30 min period of stirring, during which Compound 3 is precipitated as a colorless solid, the reaction mixture is diluted with hexane, and the solvent is removed by filtration (or trituration on small scale).

Alternatively, the purified Compound 2 (34.3 g (64.12 mmol)) was dissolved in 31.4 ml (4 equiv, 256.49 mmol) of paraldehyde. 0.3 ml of TMS-triflimide (1 mol %, 0.064 mmol) catalyst was added at room temperature. After a 30 min period of stirring, Compound 3 precipitated as a colorless solid, and the reaction mixture was diluted with hexane (100 ml). The solvent was removed by filtration, and Compound 3 was washed with hexane (10 ml×3) and dried. Compound 3 (11.31 g) was used in the next step without further purification.

The progress of the reaction was monitored by TLC (2/8 of EtOAc/Hexanes). TLC analysis of the hexane mother filtrate was also performed; significant amount of aldol product was found in the hexane filtrate.

Example 3: Preparation of Compound 4

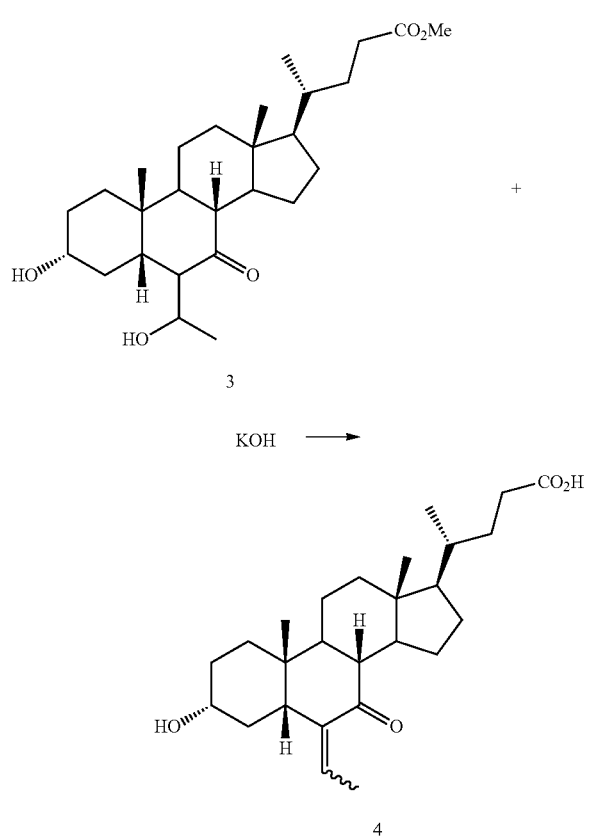

In the saponification step, 40 ml of 1:1 (v/v) water and ethanol was added to 10.8 g (21.28 mmol) of Compound 3. KOH (3.0 equiv, 3.58 g, 63.84 mmol) was added to the reaction mixture at room temperature. The reaction mixture was heated. The progress of the reaction was monitored by TLC. After 30 min, the reaction mixture was allowed to cool to room temperature and transferred into a separator funnel. The reaction was extracted with MTBE (30 mL). The resulting aqueous phase was acidified using 2 N aq. HCl (40 ml) until a pH below 3 was obtained. Extraction with MTBE (3×30 mL), followed by drying the organic phase over $Na_2SO_4$ (3 g), and removal of the solvent afforded Compound 4.

Alternatively Compound 3 (0.944 g, 1.86 mmol) is dissolved in a mixture of EtOH and water (1/1 v:v, 4 mL), and KOH (2.5 equiv, 0.281 g, 4.65 mmol) is added. The resulting reaction mixture is heated for a period of 2 h. After full conversion, Compound 4 is observed by TLC. The reaction mixture is allowed to cool to room temperature and transferred into a separator funnel. After diluting with water (3 mL), the reaction is extracted with MTBE (5 mL). The resulting aqueous phase is acidified using 10% aq. HCl until a pH below 3 is obtained. Compound 4 is extracted with MTBE (3×5 mL) as off white foam after concentration (0.826 g, 77% rel. to purified silyl enol ether, 67% rel. to crude silyl enol ether).

Example 4: Preparation of Compound 5

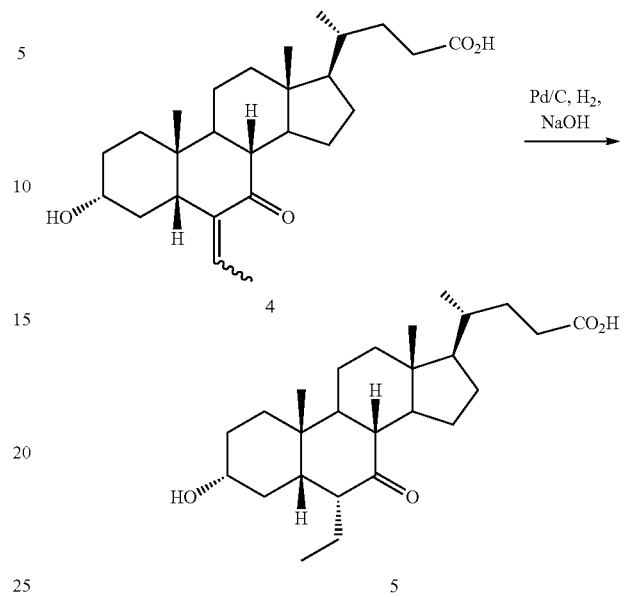

A solution of Compound 4 in aqueous NaOH is contacted with palladium on carbon and pressurized with 2-bar hydrogen pressure. The mixture is vigorously stirred and heated until hydrogen uptake ends. The mixture is filtered through Celite and the aqueous layer is contacted with dilute aqueous HCl in the presence of n-butyl acetate. The organic layer is separated and partially evaporated to induce crystallization. The suspension is filtered and the solids are washed with n-butyl acetate to afford Compound 5.

Example 5: Preparation of OCA

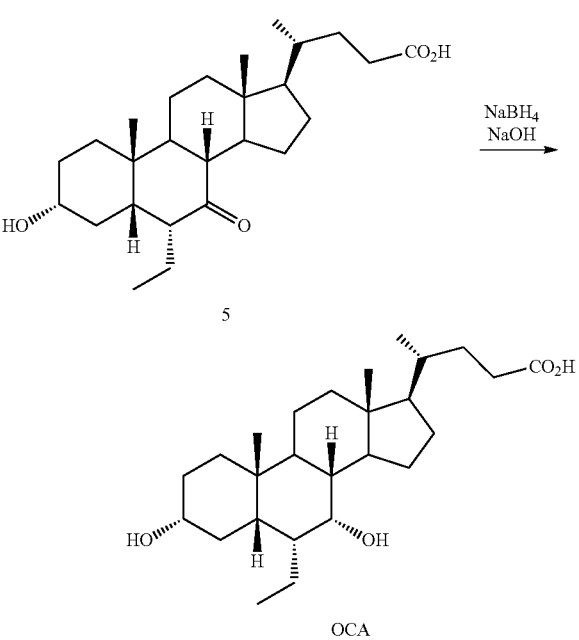

A solution of Compound 5 in aqueous NaOH is heated to 90° C. and contacted with sodium borohydride. The mixture is cooled and quenched with an aqueous citric acid solution in the presence of n-butyl acetate. The organic layer is separated and partially evaporated to induce crystallization. The suspension is filtered and the solids are washed with n-butyl acetate to afford OCA.

Example 6: Preparation of Compound 6

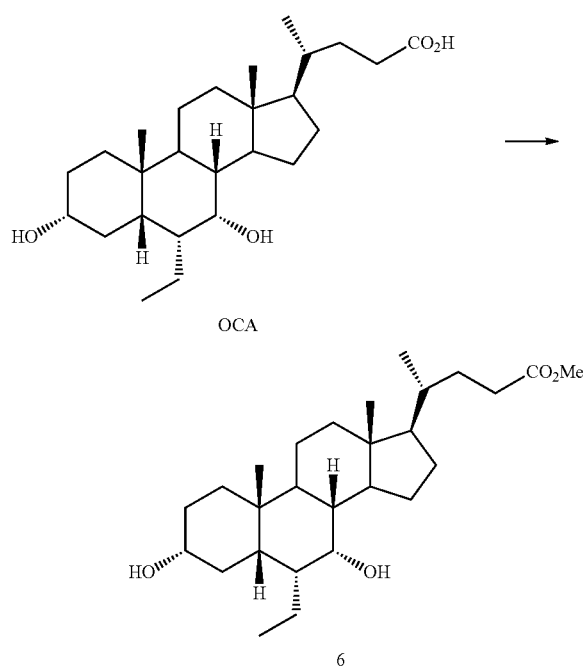

OCA

6 p-Toluenesulfonic acid monohydrate is added to a stirring solution of OCA in methanol and the reaction mixture is sonicated until complete disappearance of OCA, which takes approximately 3 hr. The solvent is evaporated under vacuum and the resulting residue is dissolved in methylene chloride, and washed with a saturated aqueous solution of sodium bicarbonate, water, and brine. The combined organic layers are dried over anhydrous sodium sulfate, and the solvent is evaporated under vacuum to afford Compound 6.

Example 7: Preparation of Compound 7

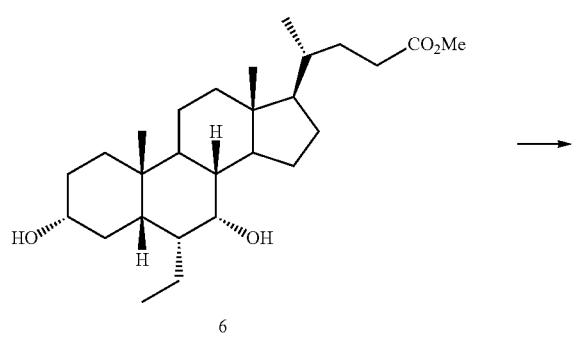

6

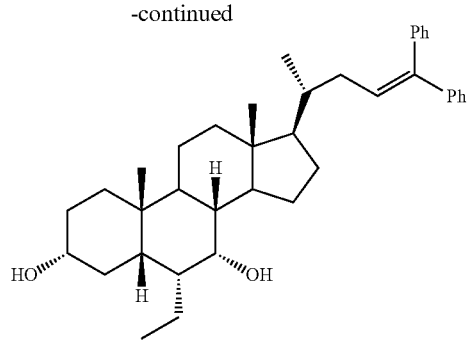

7

Compound 6 is dissolved in freshly distilled THF and the resulting mixture is warmed with stirring under a nitrogen atmosphere. Phenylmagnesiumbromide 1M in THF is added dropwise and the resulting mixture is stirred at the same temperature overnight. The reaction mixture is allowed to cool to room temperature and cyclohexane is added. The reaction mixture is filtered and the gum-solid residue is dissolved in a mixture of 3 N hydrochloric acid solution and DCM. The resulting mixture is stirred for 30 min. The organic phase is separated, and the aqueous phase is extracted with DCM. The combined organic layers are washed with brine, dried over $Na_2SO_4$, and the solvent is evaporated under vacuum. The crude residue is taken in DCM, washed with a saturated solution of sodium bicarbonate, water, brine, dried over anhydrous sodium sulfate and concentrated in-vacuo to afford Compound 7.

Example 8: Preparation of Compound 8

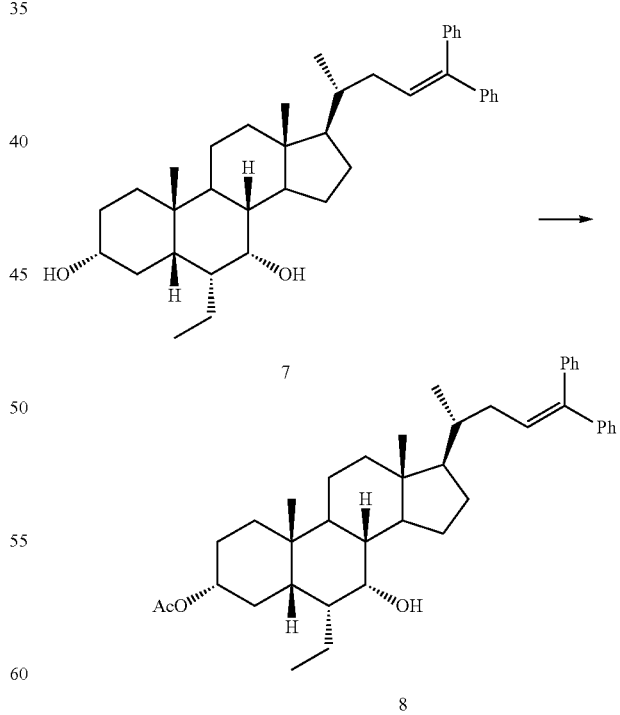

7

8

Acetic anhydride, pyridine, and 4-dimethylaminopyridine are added to a stirring solution of Compound 7 in freshly distilled THF. The reaction mixture is kept at room temperature overnight. The reaction mixture is diluted with water and extracted with DCM. The combined organic layers are washed with brine, dried over anhydrous sodium sulfate and the solvent is evaporated to afford Compound 8.

Example 9: Preparation of Compound 9

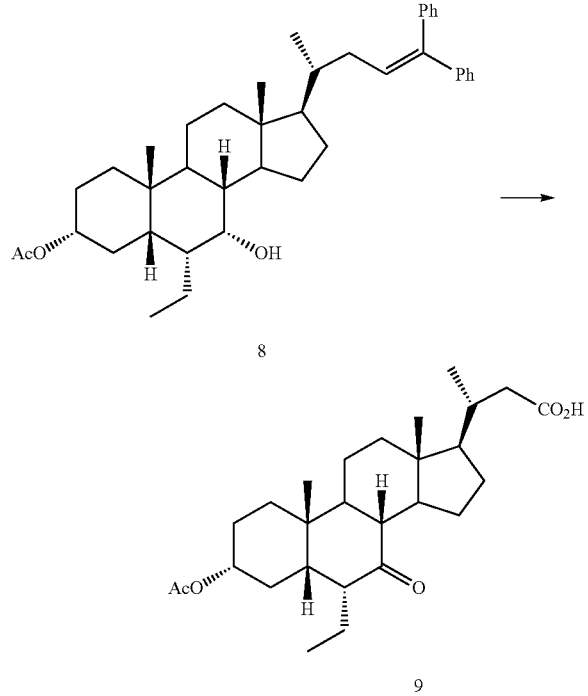

8

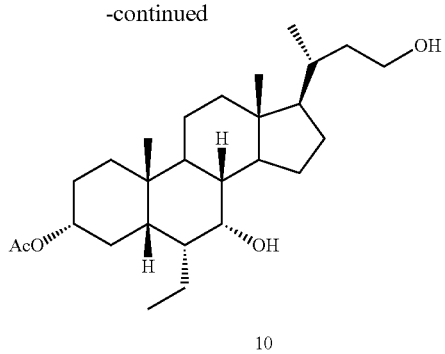

NaIO$_4$ is stirred in H$_2$O and 2N H$_2$SO$_4$. After 15 min, the reaction mixture is cooled to 0° C. and RuCl$_3$ is added. The reaction mixture is stirred until the color turned into bright yellow. Ethyl acetate and acetonitrile are added and the resulting reaction mixture is stirred for 5 min. Compound 8 is added to the reaction mixture at 0° C., and stirred until Compound 8 is consumed. The reaction mixture is filtered, poured into H$_2$O and extracted with ethyl acetate. The combined organic layers are washed with a saturated solution of Na$_2$S$_2$O$_3$, dried over anhydrous Na$_2$SO$_4$ and concentrated under vacuum. The resulting residue is purified by flash chromatography to afford Compound 9 as a white solid.

Example 10: Preparation of Compound 10

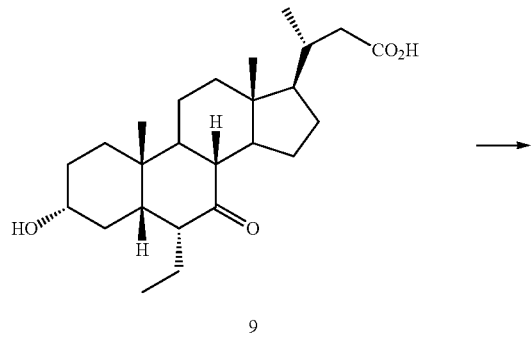

9

Triethylamine is added to a stirring ice-cooled solution of Compound 9 and isobutyl chloroformate in THF. After 1 hr, the reaction mixture is filtered under vacuum in an argon atmosphere. The resulting solution is treated with sodium borohydride for 1 hr at 0° C., which is added in portions. The reaction mixture is quenched with H$_2$O, stirred for additional 2 hr at room temperature, acidified with 3N hydrochloric acid and extracted with ethyl acetate. The combined organic extracts are washed with brine, dried over anhydrous Na$_2$SO$_4$, and concentrated under vacuum to afford Compound 10.

Example 11: Preparation of Compound 11 (Sodium Salt)

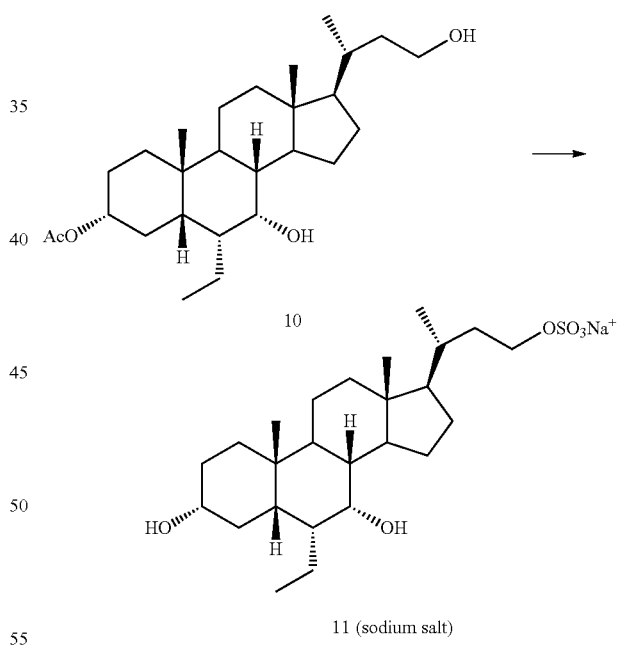

11 (sodium salt)

Compound 10 is added to a suspension of sulfur trioxide pyridine complex in dry pyridine (60 mL) and allowed to react at room temperature under nitrogen atmosphere for 24 hr. The solvent is evaporated, and the resulting residue is dissolved in methanol and treated with a 10%, (w/w) solution of NaOH in MeOH. The reaction mixture is refluxed overnight. The solvent is evaporated and the resulting white solid is dissolved in a H$_2$O/MeOH solution and passed through a NaOH activated Dowex resin, eluting first with H$_2$O and then with a solution of H$_2$O/MeOH. The fractions containing the sodium salt of Compound 11 are evaporated to dryness and the resulting solid is purified via a reverse phase column RP-18 (Lobar C), using a $H_2O$/MeOH mixture as mobile phase.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A method of preparing obeticholic acid (OCA)

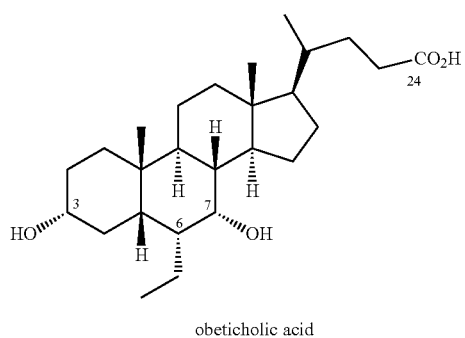

obeticholic acid or a pharmaceutically acceptable salt, solvate, or amino acid conjugate thereof, comprising:
a) reacting Compound 2 with paraldehyde to form Compound 3:

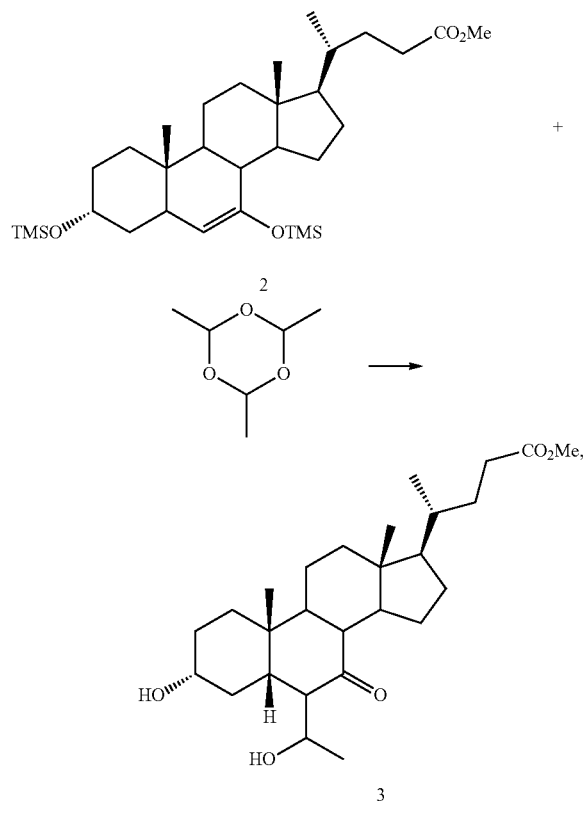

wherein the reaction is conducted at a temperature between 10° C. and 30° C.,
b) reacting Compound 3 with a base to form Compound 4:

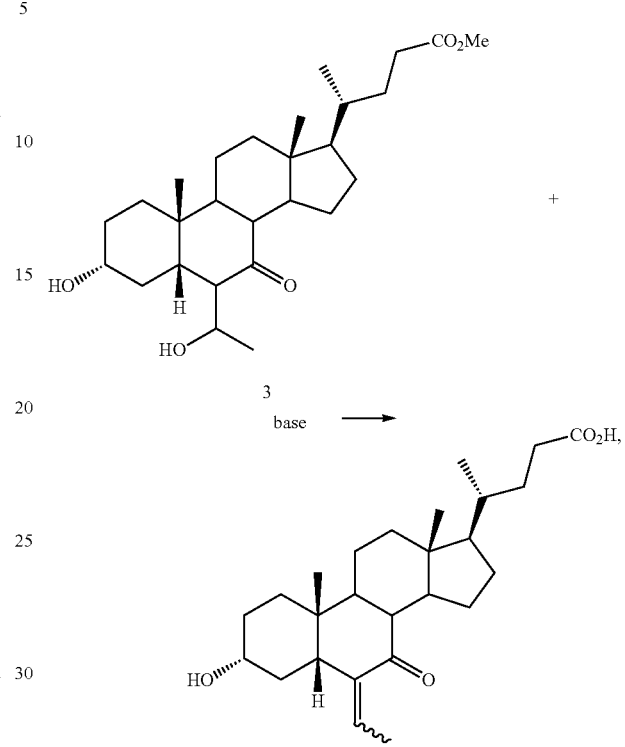

c) hydrogenating Compound 4 to form Compound 5:

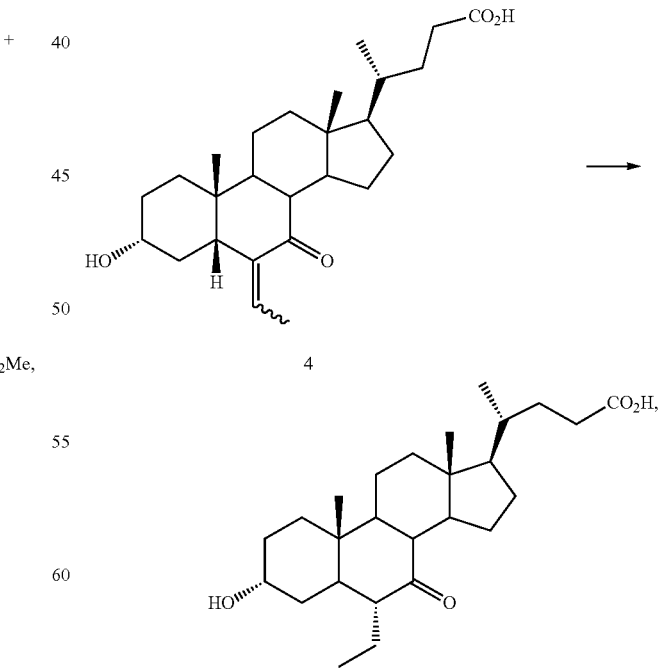

and d) reducing the keto group at the C-7 position of Compound 5 to form OCA:

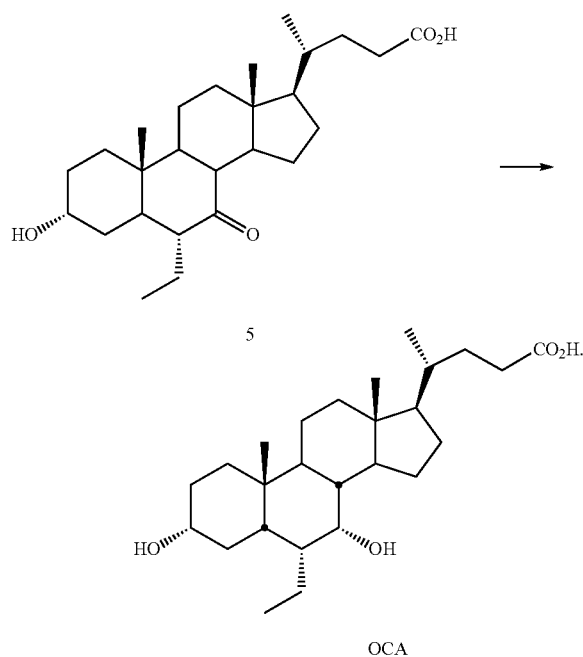

2. A method of claim 1, wherein reacting Compound 2 with paraldehyde to form Compound 3 is conducted in the presence of a triflimide catalyst:

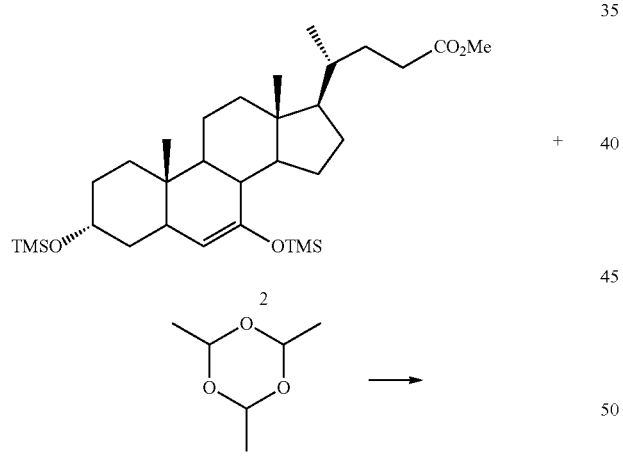

3. The method of claim 2, wherein the triflimide catalyst is selected from $(Tf)_2NH$, $(Tf)_2N—(C_1-C_3$ alkyl), and $(Tf)_2N$-tri-$C_1$-$C_3$ alkylsilyl.

4. The method of claim 3, wherein the triflimide catalyst is $(Tf)_2N$-trimethylsilyl.

5. The method of claim 1, wherein the reaction of Compound 2 with paraldehyde to form Compound 3 is conducted in neat paraldehyde:

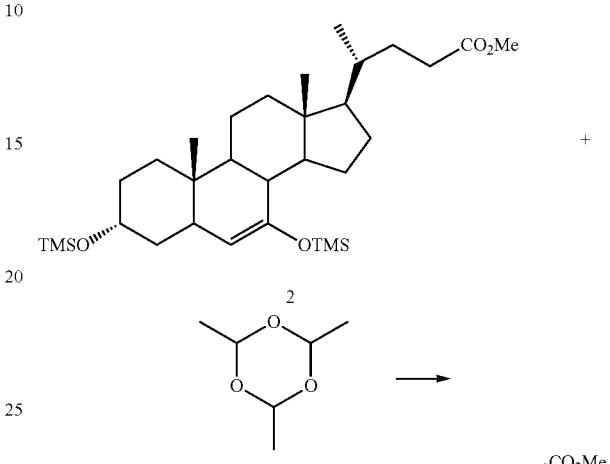

6. The method of claim 1, wherein the molar ratio of paraldehyde to Compound 2 is between 3:1 and 6:1.

7. The method of claim 2, wherein the reaction is conducted for 10 min to 4 hr.

8. The method of claim 1, wherein Compound 3 is reacted with a base selected from metal hydroxide, $C_1$-$C_6$ alkoxide, and metal hydride to form Compound 4:

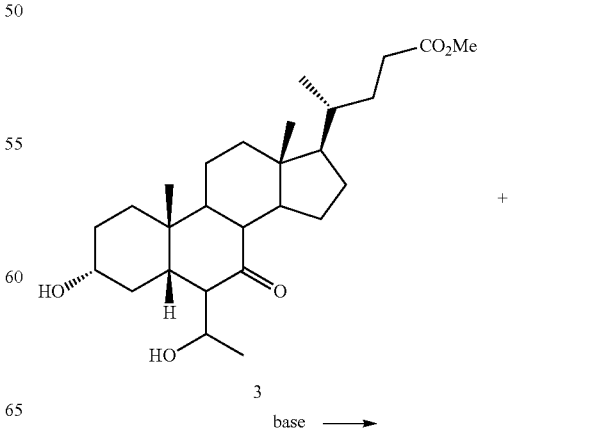

-continued

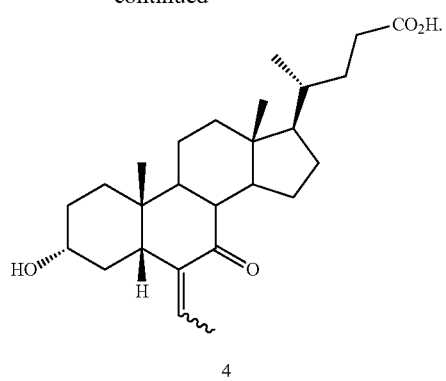

4

9. The method of claim 8, wherein the metal hydroxide is sodium hydroxide or potassium hydroxide.

10. The method of claim 9, wherein the metal hydroxide is potassium hydroxide.

11. The method of claim 8, wherein the reaction is conducted in a solvent selected from methanol, ethanol, propanol, isopropanol, water, and a mixture thereof.

12. The method of claim 11, wherein the solvent is a mixture of ethanol and water, at an ethanol/water ratio of between 1:3 to 3:1 (vol/vol).

13. The method of claim 1, wherein hydrogenating Compound 4 to form Compound 5 is conducted in the presence of a palladium catalyst:

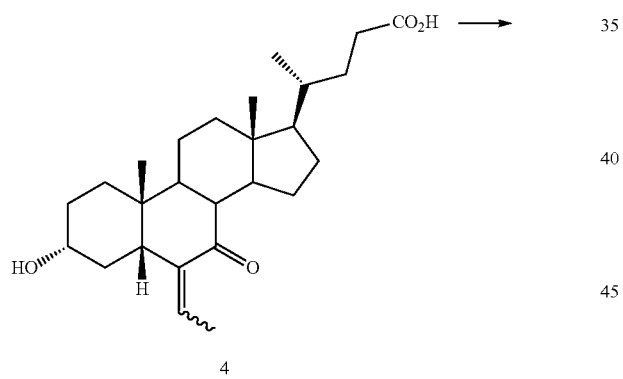

4

5

14. The method of claim 1, wherein reducing the keto group at the C-position of Compound 5 is conducted with sodium borohydride or sodium triacetoxyborohydride to form OCA:

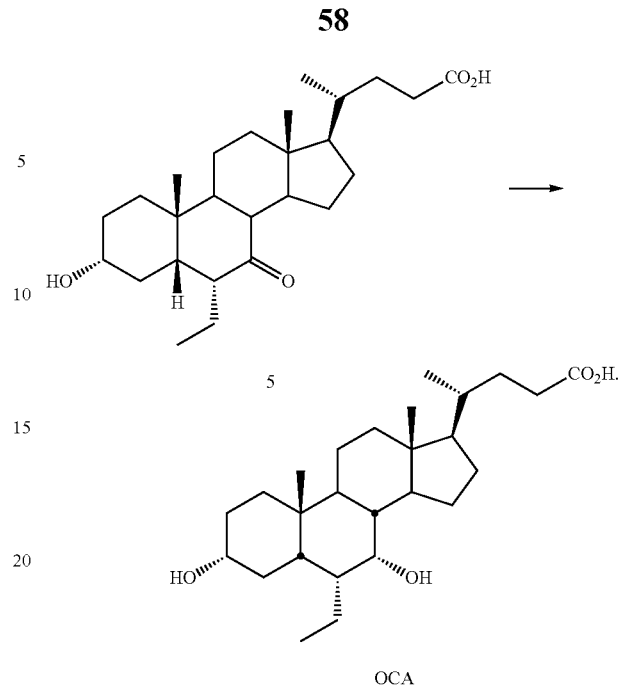

5

OCA

15. The method of claim 1, further comprising reacting Compound 1 with an alkyl silyl halide to form Compound 2:

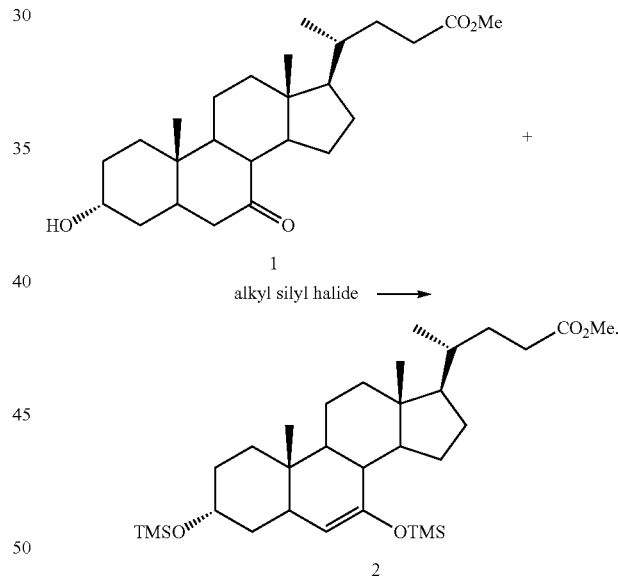

1 alkyl silyl halide ⟶

2

16. The method of claim 15, further comprising esterifying 7-keto lithocholic acid (KLCA) to form Compound 1:

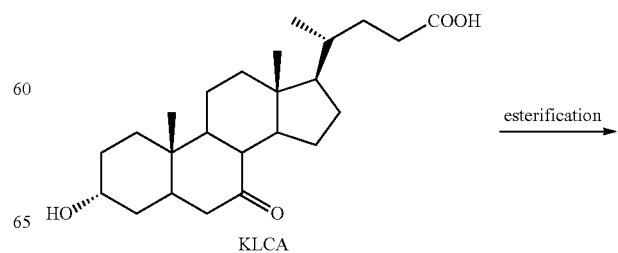

KLCA esterification ⟶

-continued

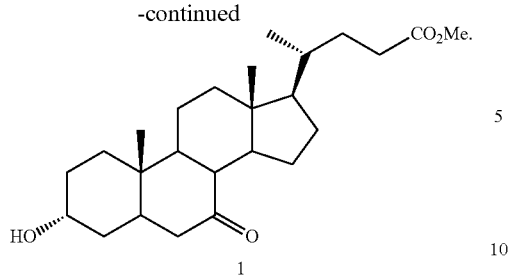

1

17. The method of claim 12, wherein the solvent is a mixture of ethanol and water, at an ethanol/water ratio of between 1:2 to 2:1 (vol/vol).

18. The method of claim 17, wherein the solvent is a mixture of ethanol and water, at an ethanol/water ratio of between 1:1.5 to 1.5:1 (vol/vol).

19. The method of claim 18, wherein the solvent is a mixture of ethanol and water, at an ethanol/water ratio of between 1:1.2 to 1.2:1 (vol/vol).

20. The method of claim 19, wherein the solvent is a mixture of ethanol and water, at an ethanol/water ratio of between 1:1 to 1:1 (vol/vol).

* * * * *